(12) United States Patent
Mainkar et al.

(10) Patent No.: US 11,306,100 B2
(45) Date of Patent: Apr. 19, 2022

(54) SPIROOXINDOLE COMPOUNDS AS GSK3B INHIBITORS AND PROCESS FOR PREPARATION THEREOF

(71) Applicant: COUNCIL OF SCIENTIFIC & INDUSTRIAL RESEARCH, New Delhi (IN)

(72) Inventors: Prathama S. Mainkar, Telangana (IN); Mohammad Abdul Sattar, Telangana (IN); Pitchakuntla Mallesham, Telangana (IN); Togapur Pavan Kumar, Telangana (IN); Divya Duscharla, Telangana (IN); Ummanni Ramesh, Telangana (IN); Srivari Chandrasekhar, Telangana (IN)

(*) Notice: Subject to any disclaimer, the term of this patent is extended or adjusted under 35 U.S.C. 154(b) by 254 days.

(21) Appl. No.: 16/492,359

(22) PCT Filed: Mar. 9, 2018

(86) PCT No.: PCT/IN2018/050134
§ 371 (c)(1),
(2) Date: Sep. 9, 2019

(87) PCT Pub. No.: WO2018/163216
PCT Pub. Date: Sep. 13, 2018

(65) Prior Publication Data
US 2021/0284650 A1 Sep. 16, 2021

(30) Foreign Application Priority Data
Mar. 10, 2017 (IN) .............................. 201611008487

(51) Int. Cl.
*C07D 491/107* (2006.01)
*A61P 35/00* (2006.01)

(52) U.S. Cl.
CPC .......... *C07D 491/107* (2013.01); *A61P 35/00* (2018.01)

(58) Field of Classification Search
CPC ................................................. C07D 491/107
See application file for complete search history.

(56) References Cited

U.S. PATENT DOCUMENTS

| | | | |
|---|---|---|---|
| 6,358,750 B1 | 3/2002 | Fokas et al. | |
| 6,774,132 B1 | 8/2004 | Claesson et al. | |
| 8,101,647 B2 | 1/2012 | Chafeev et al. | |
| 8,742,109 B2 | 6/2014 | Cadieux et al. | |
| 8,962,828 B2 | 2/2015 | Karig et al. | |
| 2010/0004190 A1 | 1/2010 | Chan et al. | |
| 2010/0105745 A1 | 4/2010 | Minamoto | |

FOREIGN PATENT DOCUMENTS

| EP | 0278352 A2 | 8/1998 |
|---|---|---|
| EP | 1557417 A1 | 7/2005 |
| EP | 2488531 B1 | 8/2012 |
| WO | 2009073620 A2 | 6/2009 |
| WO | 2010045251 A2 | 4/2010 |
| WO | 2011002708 A1 | 1/2011 |
| WO | 2011047174 A1 | 4/2011 |
| WO | 2014058035 A1 | 4/2014 |

OTHER PUBLICATIONS

Walz; Clin Cancer Res; 2017, 23, 1891-1897. (Year: 2017).*
Anada, et al., "A New Dirhodium(II) Carboxamidate Complex as a Chiral Lewis Acid Catalyst for Enantioselective Hetero-Diels-Alder Reactions," Angew. Chem., 116:2719-2722 (2004).
Ding, et al., "Structure-Based Design of Spiro-oxindoles as Potent, Specific Small-Molecule Inhibitors of the MDM2-p53 Interaction," J. Med. Chem., 49:3432-3435 (2006).

(Continued)

*Primary Examiner* — Daniel R Carcanague
(74) *Attorney, Agent, or Firm* — Abelman, Frayne & Schwab; Stefan Knirr

(57) ABSTRACT

The present invention provides a compound of general formulae I useful as GSK3β inhibitors and their anticancer potential and process for preparation of these spirooxindoles.

Formula I

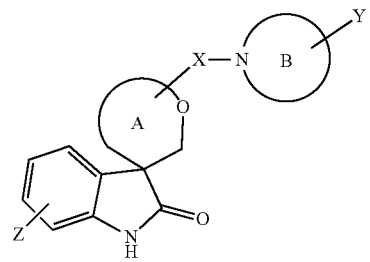

wherein

Z is hydrogen, halogen, hydroxy, alkoxy, cyano, nitro;

Ring A is a five membered or six membered or seven membered optionally containing additional hetero atom in the ring X is optionally CH$_2$ Ring B is triazole or cyclic amine alone or with one or more hetero atoms part of the ring and optionally substituted with one or more substituents Y is hydrogen, alkoxy, aryloxy, hydroxy, ester, amide, amino, alkyl or aryl, heteroaryl, wherein these substituents are optionally substituted with one or more halogen, hydroxy, alkoxy, alkyl, aryl, heteroaryl, aryloxy, nitro, cyano, ester, aldehyde, wherein these substituents are further substituted with one or more halogen, hydroxy, alkoxy, alkyl, aryl, heteroaryl, aryloxy, nitro, cyano, ester, aldehyde.

10 Claims, 8 Drawing Sheets

(56) References Cited

OTHER PUBLICATIONS

Hong, et al., "Recent Advances in Asymmetric Organocatalytic Construction of 3,3'-Spirocyclic Oxindoles," Adv. Synth. Catal., 355:1023-1052 (2013).

Jiang, et al., "Design, synthesis and biological evaluations of novel oxindoles as HIV-1 non-nucleoside reverse transcriptase inhibitors. Part I." Bioorg. Med. Chem. Lett., 16:2105-2108 (2006).

Katsoulis, et al., "Synthesis of 5,6-Spiroethers and Evaluation of their Affinities for the Bacterial A Site," ChemBioChem., 12:1188-1192 (2016).

Kornet, et al., "Oxindole-3-spiropyrrolidines and -piperidines. Synthesis and Local Anesthetic Activity," J. Med. Chem., 19(7):892-898 (1976).

Malhotra, et al., "Design, synthesis and biological activity evaluation of regioisomeric spiro-(indoline-isoxazolidines) in the inhibition of TNF-α-induced ICAM-1 expression on human endothelial cells," Med. Chem. Comm., 3:1536-1547 (2012).

Wang, et al., "Highly Steroselective Brønsted Acid Catalyzed Synthesis of Spirooxindole Pyrans, " Org. Letters, 12:3086-3089 (2011).

Zhu, et al., "Enantioselective Construction of Spirocyclic Oxindole Derivatives with Multiple Stereocenters via an Organocatalytic Michael/Aldol/Hemiacetalization Cascade Reaction, " Org. Lett., 18:2387-2390 (2016).

Chemical Abstract Accession No. 1691090-70-6—May 24, 2015.
Chemical Abstract Accession No. 1694142-26-1—Apr. 29, 2015.
Chemical Abstract Accession No. 1699579-55-9—May 6, 2015.
Chemical Abstract Accession No. 1702718-68-0—May 13, 2015.
Chemical Abstract Accession No. 1969003-24-4—Aug. 8. 2016.
Chemical Abstract Accession No. 1989963-10-1—Sep. 9, 2016.
Chemical Abstract Accession No. 2059927-67-0—Jan. 26, 2017.
Chemical Abstract Accession No. 2060027-64-5—Jan. 27, 2017.

* cited by examiner

SPIROOXINDOLE COMPOUNDS AS GSK3B INHIBITORS AND PROCESS FOR PREPARATION THEREOF

RELATED APPLICATIONS

This application is a national phase of International Application No, PCT/IN2018/050134 filed Mar. 9, 2018 and claims priority from Indian Patent Application No. 201611008487 filed Mar. 10, 2017, both incorporated by reference in their entirety.

FIELD OF THE INVENTION

The present invention relates to spirooxindole compounds useful as GSK3β inhibitors and process for preparation thereof. Particularly the present invention relates to spirooxindole compounds of general formula 1.

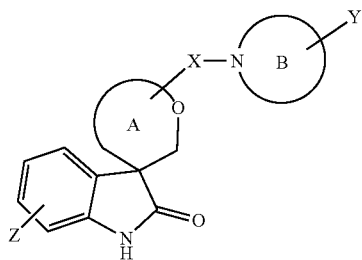

Formula I wherein
Z is hydrogen, halogen, hydroxy, alkoxy, cyano, nitro;
Ring A is a five membered or six membered or seven membered optionally containing additional hetero atom in the ring
X is optionally $CH_2$
Ring B is triazole or cyclic amine alone or with one or more hetero atoms part of the ring and optionally substituted with one or more substituents
Y is hydrogen, alkoxy, aryloxy, hydroxy, ester, amide, amino, alkyl or aryl, heteroaryl, wherein these substituents are optionally substituted with one or more halogen, hydroxy, alkoxy, alkyl, aryl, heteroaryl, aryloxy, nitro, cyano, ester, aldehyde,
wherein these substituents are further substituted with one or more halogen, hydroxy, alkoxy, alkyl, aryl, heteroaryl, aryloxy, nitro, cyano, ester, aldehyde;

BACKGROUND OF THE INVENTION

Oxindoles substituted in the 3 position are an important structural motif among a series of natural substances and pharmaceutically effective substances. Some of these compounds exhibit biological activity against various pathogens and have e.g. antitumor or anti-HIV properties (J. Med. Chem. 2006, 49, 3432; Bioorg. Med. Chem. Lett. 2006, 16, 2105). Among the 3-substituted oxindoles, spirocyclic oxindoles are the structural motifs frequently found in many natural products and biologically active molecules. The key structural characteristic of these compounds is the spiro ring fused at the 3-position of the oxindole core, with varying degrees of substitution around it. The alkaloids such as mitraphylline, pteropodine, gelsemine, speciophylline, uncarine, Strychnofoline, Alstonisine, Rhychnophylline, Spirotriprostatin A, Salacin, Elocamine, Horsifiline, Coerulesine etc., are some of the example of natural products containing spirooxindole structural framework. Spirooxindole derivatives were found to exhibit good biological properties (PCT Patent Application No. WO 2006/110917, WO 2010/45251, WO 2014/058035, WO 2011/047174; PCT/US2010/040187; EP 2488531, U.S. Pat. Nos. 8,101,647, 8,742,109, 6,358,750, 8,962,828). These are useful for the treatment of sodium-channel mediated diseases, diseases related to pain, central nervous conditions (such as epilepsy, anxiety, depression and bipolar disease), cardiovascular conditions (such as arrhythmias, atrial fibrillation and ventricular fibrillation), neuromuscular conditions such as (restless syndrome, neuroprotection against stroke, neural trauma, and multiple sclerosis), channelopathesis such as erythromelalgia and familial rectal pain syndrome. Certain spirooxindoles were also found to exhibit good analgesic and anesthetic properties (J. Med. Chem. 1976, 19, 892) and are particularly effective in treatment of chronic pain (U.S. Pat. No. 6,774,132). Spirooxindole compounds are also used as aldose reductase inhibitors and are used in the treatment of diabetes. It is not surprising that these compounds have been the focus of many chemists, in part because of their biological activities, but also the challenge of the simultaneous creation of spiro-quaternary centers and multiple chiral centers. As a result, numerous elegant transformations have been developed for the effective construction of these structural skeletons (Adv. Synth. Catal. 2013, 355, 1023; Org. Lett. 2011, 13, 3086; Angew. Chem. 2004, 116, 2719). Although many types of spirooxindole derivatives were reported using a variety of strategies toward the construction of spirooxindole architecture, there are certain groups of spirooxindole architecture of interest that have not been synthesized and evaluated for biological properties. Spirooxindole-triazoles and spirooxindole-cyclic amines are examples of this kind and are impossible to find naturally. Therefore, there is a need for the development of methods for the synthesis and biological evaluation of diversely substituted spirooxindoles containing triazole and cyclic amine motifs and others.

In this context a large number of new spirooxindoles architectures possessing triazole and cyclic amines have been synthesized and evaluated for GSK3β activity and their anticancer potential.

OBJECTIVE OF THE INVENTION

The main objective of the present invention is to provide novel spirooxindole compounds as useful GSK3β inhibitors.

Another objective of the present invention is to provide the process for the preparation of novel spirooxindoles compounds.

SUMMARY OF THE INVENTION

The above and other objectives of the present invention are achieved by providing the new spirooxindole compounds, which have been synthesized from oxindole.

Accordingly, the present invention affords a new class of spirooxindole of general formula I.

Formula I

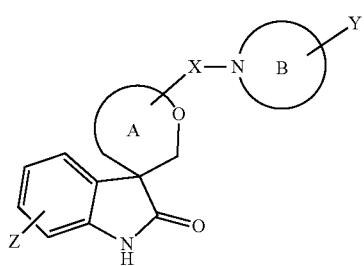

wherein

Z is hydrogen, halogen, hydroxy, alkoxy, cyano, nitro;

Ring A is a five membered or six membered or seven membered optionally containing additional hetero atom in the ring X is optionally $CH_2$ or none Ring B is triazole or cyclic amine alone or with one or more hetero atoms part of the ring and optionally substituted with one or more substituents or no B ring present Y is hydrogen, halogen, azide, alkoxy, aryloxy, hydroxy, ester, amide, amino, alkyl or aryl, heteroaryl, wherein these substituents are optionally substituted with one or more halogen, hydroxy, alkoxy, alkyl, aryl, heteroaryl, aryloxy, nitro, cyano, ester, aldehyde, wherein these substituents are further substituted with one or more halogen, hydroxy, alkoxy, alkyl, aryl, heteroaryl, aryloxy, nitro, cyano, ester, aldehyde;

The structural formulas of the representative compounds are

Formula II

9a

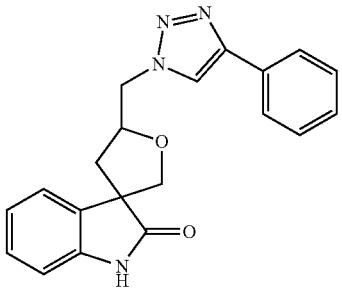

wherein the example of specific compounds are as follows

Formula III

AB-E

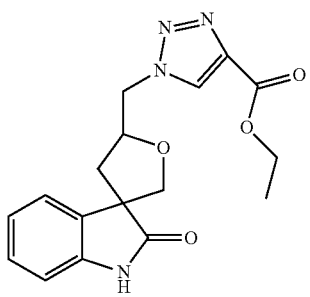

AB-C

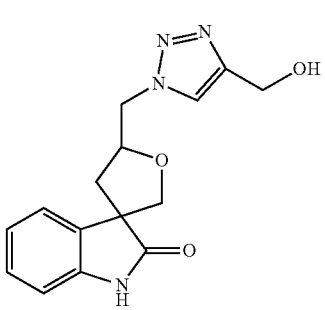

AB-G

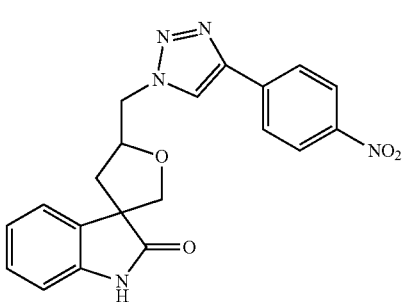

AB-D

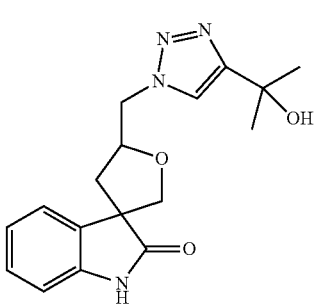

AB-E

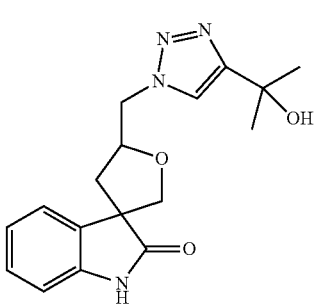

AB-P

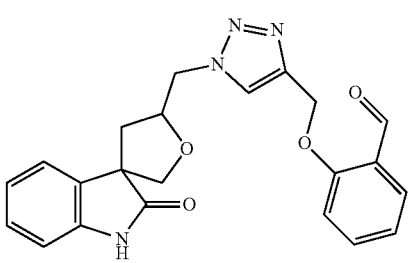

-continued
AB-O
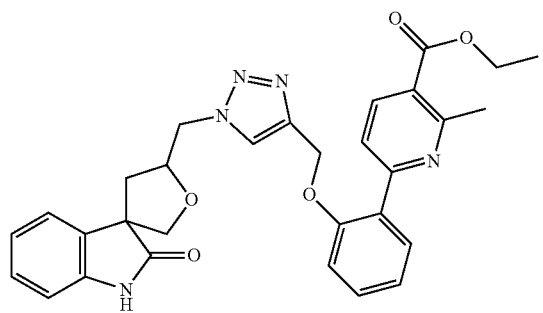
wherein the example of specific compounds are as follows
Formula IV
AB-K
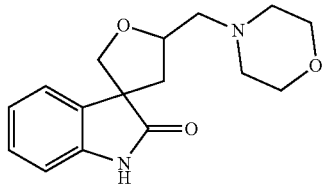
AB-M
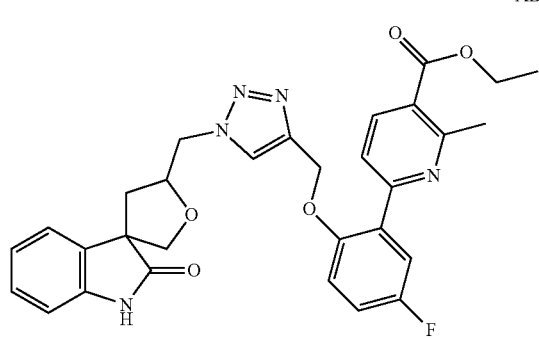
AB-X
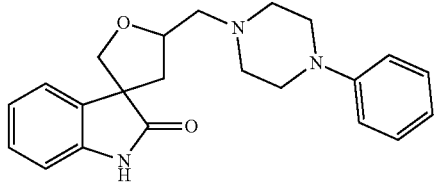
AB-T
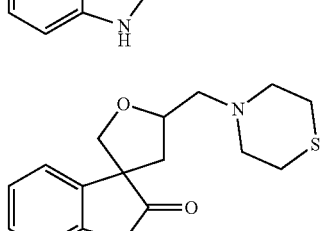
AB-W
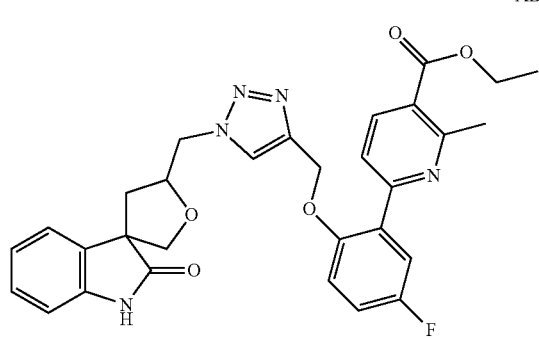
AB-L
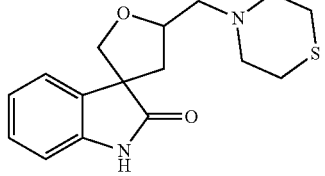
AB-N
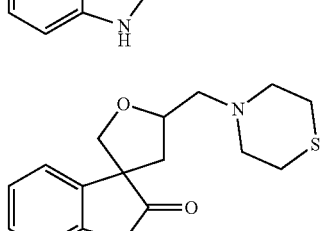
AB-S
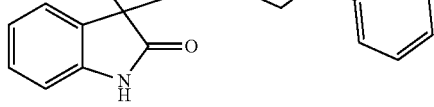
AB-U
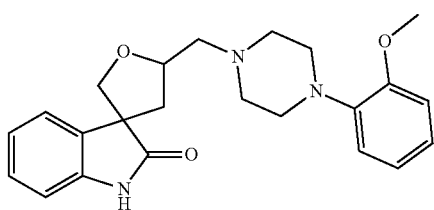
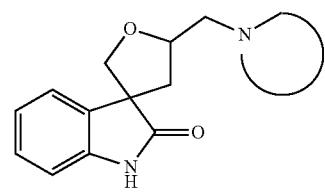
AB-R
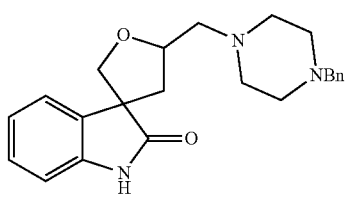

AB-Q
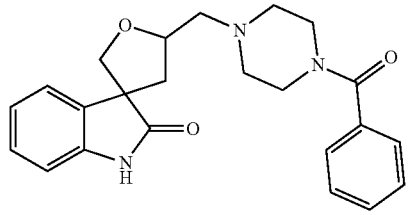
AB-V
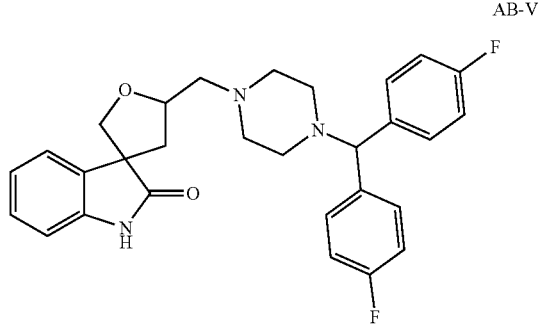
9b
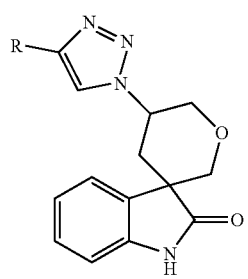
wherein the example of specific compounds are as follow
AC-A
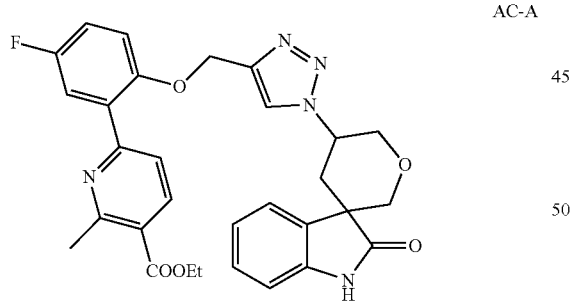
AC-B
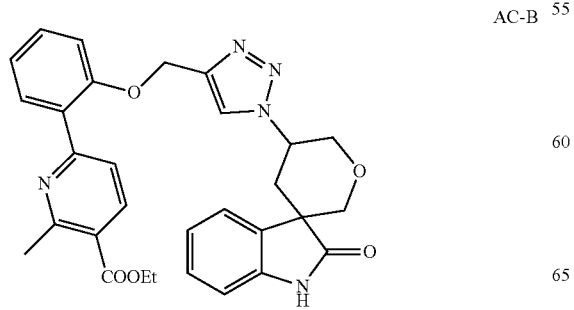
AC-C
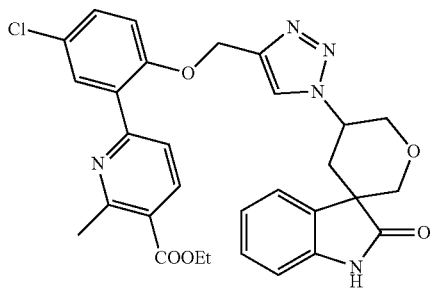
AC-D
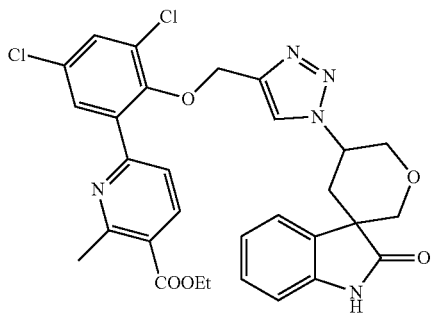
AC-E
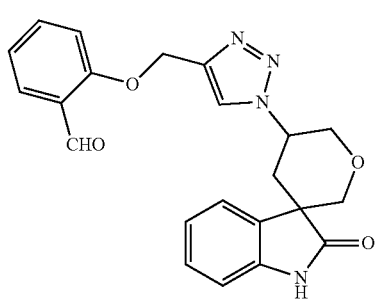
AC-F
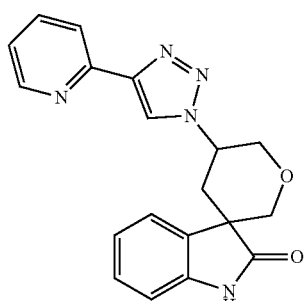
AC-G
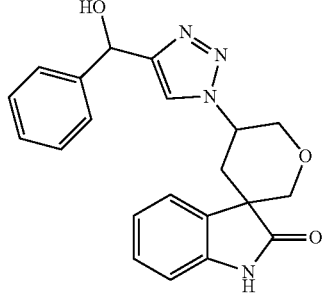

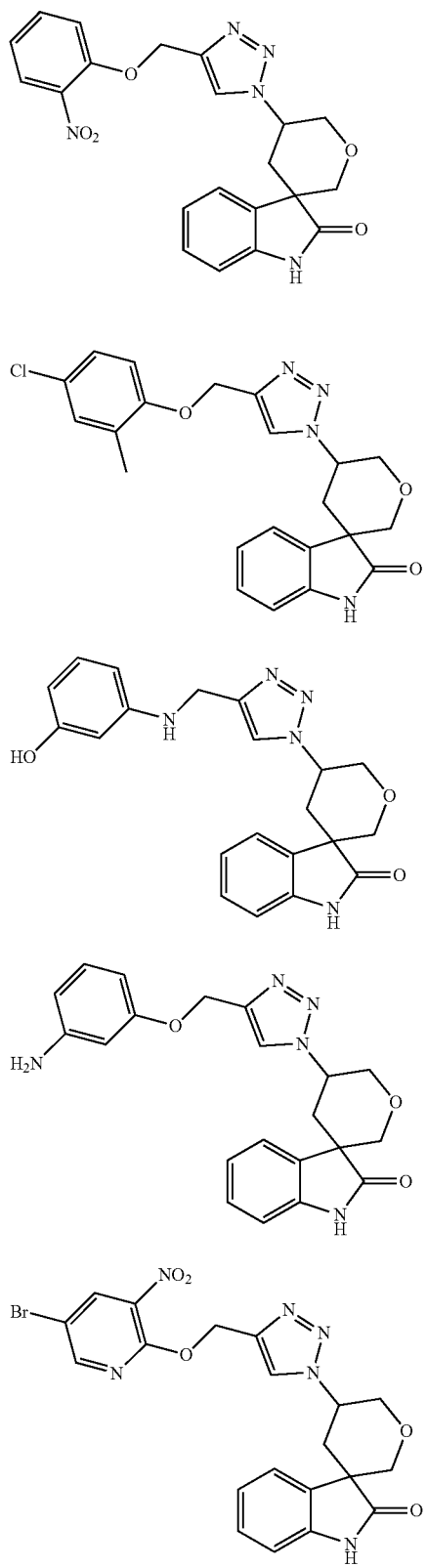

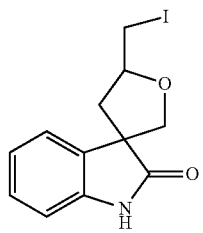

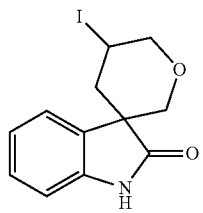

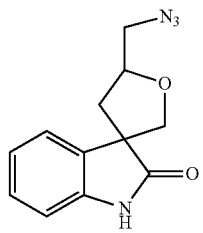

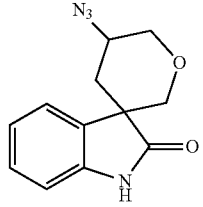

Structures of the other intermediated compounds in the process for the preparation of spirooxindole derivatives are represented as In an embodiment of the present invention, the novel spirooxindole derivatives described herein are represented by (AC-A) Ethyl 6-(5-fluoro-2-((1-(2-oxo-2', 4', 5', 6'-tetrahydrospiro[indoline-3,3'-pyran]-5'-yl)-1H-1,2,3-triazol-4-yl)methoxy)-phenyl)-2-methylnicotinate (AC-B) Ethyl 2-methyl-6-(2-((1-(2-oxo-2',4',5',6'-tetrahydrospiro[indoline-3,3'-pyran]-5'-yl)-1H-1,2,3-triazol-4-yl)methoxy)-phenyl)nicotinate (AC-C) Ethyl 6-(5-chloro-2-((1-(2-oxo-2',4',5',6'-tetrahydrospiro [indoline-3,3'-pyran]-5'-yl)-1H-1,2,3-triazol-4-yl)methoxy)-phenyl)-2-methyl nicotinate (AC-D) Ethyl 6-(3,5-dichloro-2-((1-(2-oxo-2',4',5',6'-tetrahydrospiro-[indoline-3,3'-pyran]-5'-yl)-1H-1,2,3-triazol-4-yl)methoxy)phenyl)-2-methyl nicotinate (AC-E) 2-((1-(2-oxo-2', 4', 5', 6'-tetrahydrospiro[indoline-3, 3'-pyran]-5'-yl)-1H-1,2,3-triazol-4-yl) methoxy)benzaldehyde (AC-F) 5'-(4-(pyridin-2-yl)-1H-1,2,3-triazol-1-yl)-2',4',5', 6'-tetrahydrospiro[indoline-3,3'-pyran]-2-one (AC-G) 5'-(4-(hydroxy(phenyl)methyl)-1H-1,2,3-triazol-1-yl)-2',4',5',6'-tetrahydrospiro [indoline-3,3'-pyran]-2-one (AC-H) 5'-(4-((2-nitrophenoxy)methyl)-1H-1,2,3-triazol-1-yl)-2',4',5',6'-tetrahydrospiro-[indoline-3,3'-pyran]-2-one (AC-I) 5'-(4-((4-chloro-2-methylphenoxy)methyl)-1H-1,2, 3-triazol-1-yl)-2',4',5',6'-tetra hydrospiro[indoline-3,3'-pyran]-2-one (AC-J) 5'-(4-((3-hydroxyphenylamino)methyl)-1H-1,2,3-triazol-1-yl)-2',4',5',6'-tetrahydro spiro[indoline-3,3'-pyran]-2-one (AC-K) 5'-(4-((3-aminophenoxy)methyl)-1H-1,2,3-triazol-1-yl)-2',4',5',6'-tetrahydro spiro[indoline-3,3'-pyran]-2-one
(AC-L) 5'-(4-((5-bromo-3-nitropyridin-2-yloxy) methyl)-1H-1,2,3-triazol-1-yl)-2',4',5',6'-tetrahydrospiro[indoline-3,3'-pyran]-2-one
(AB-O) Ethyl 2-methyl-6-(2-((1-((2'-oxo-4,5-dihydro-2H-spiro[furan-3,3'-indoline]-5-yl)methyl)-1H-1,2,3-triazol-4-yl)methoxy)phenyl)nicotinate
(AB-M) Ethyl 6-(5-fluoro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate
(AB-N) Methyl-6-(5-chloro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate
(AB-P) 2-((1-((2'-oxo-4,5-dihydro-2H-spiro[furan-3,3'-indoline]-5-yl)methyl)-1H-1,2,3-triazol-4-yl)methoxy)benzaldehyde
(AB-W) Ethyl6-(3,5-dichloro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate
(AB-F) Ethyl-1-((2'-oxo-4,5-dihydro-2H-spiro[furan-3,3'-indoline]-5-yl)methyl)-1H-1,2,3-triazole-4-carboxylate
(AB-C) 5-((4-phenyl-1H-1,2,3-triazol-1-yl)methyl)-4,5-dihydro-2H-spiro[furan-3,3'-indolin]-2'-one
(AB-G) 5-((4-(hydroxymethyl)-1H-1,2,3-triazol-1-yl)methyl)-4,5-dihydro-2H-spiro[furan-3,3'-indolin]-2'-one
(AB-E) 5-((4-(2-hydroxypropan-2-yl)-1H-1,2,3-triazol-1-yl)methyl)-4,5-dihydro-2H-spiro[furan-3,3'-indolin]-2'-one
(AB-D) 5-((4-(4-nitrophenyl)-1H-1,2,3-triazol-1-yl)methyl)-4,5-dihydro-2H-spiro[furan-3,3'-indolin]-2'-one
(AB-X) 5-((4-phenylpiperazin-1-yl)methyl)-4,5-dihydro-2H-spiro[furan-3,3'-indolin]-2'-one
(AB-K) 5-(morpholinomethyl)-4, 5-dihydro-2H-spiro[furan-3, 3'-indolin]-2'-one
(AB-S) 5-((4-(pyridin-2-yl)piperazin-1-yl)methyl)-4,5-dihydro-2H-spiro[furan-3,3'-indolin]-2'-one
(AB-U) 5-((4-(2-methoxyphenyl)piperazin-1-yl)methyl)-4,5-dihydro-2H-spiro[furan-3,3'-indolin]-2'-one
(AB-T) 5-((4-(4-methoxyphenyl)piperazin-1-yl)methyl)-4,5-dihydro-2H-spiro[furan-3,3'-indolin]-2'-one
(AB-Q) 5-((4-benzoylpiperazin-1-yl)methyl)-4,5-dihydro-2H-spiro[furan-3,3'-indolin]-2'-one
(AB-L) 5-(thiomorpholinomethyl)-4,5-dihydro-2H-spiro[furan-3,3'-indolin]-2'-one
(AB-R) 5-((4-benzylpiperazin-1-yl)methyl)-4,5-dihydro-2H-spiro[furan-3,3'-indolin]-2'-one
(AB-V) 5-((4-(bis(4-fluorophenyl)methyl)piperazin-1-yl)methyl)-4,5-dihydro-2H-spiro [furan-3,3'-indolin]-2'-one
(6a) 5-(iodomethyl)-4,5-dihydro-2H-spiro[furan-3,3'-indolin]-2'-one
(6b) 5'-Iodo-2', 4', 5', 6'-tetrahydrospiro [indoline-3,3'-pyran]-2-one
(7a) 5-(azidomethyl)-4,5-dihydro-2H-spiro[furan-3,3'-indolin]-2'-one
(7b) 5'-azido-2',4',5',6'-tetrahydrospiro[indoline-3,3'-pyran]-2-one The present invention also provides a process for the preparation of spirooxindole compounds as described in the above formula A large number of various spirooxindoles possessing diversely substituted architecture were found to exhibit several biological properties. These functionalities are prominent structural motifs of new medicines from different pharmacological groups. The development of new structural scaffolds of spirooxindole architecture is very important for the drug discovery process. In this connection a large number of spirooxindole derivatives were developed as depicted in the above general formula I to IV.

The process for the synthesis of these new spirooxindoles starts from the allylation of oxindole and involves operationally simple and highly efficient synthetic protocol giving rise to the desired products in high yields.

In an embodiment of the present invention commercially available oxindole was used as the starting material for the complete process.

In another embodiment of the present invention the first step is allylation of oxindole.

In another embodiment of the present invention the second step is protection of the free amine with Boc group.

In yet another embodiment of the present invention the third step is introduction of primary hydroxyl using formaldehyde In yet another embodiment of the present invention the fourth step is removal of the protection on free amine.

In yet another embodiment of the present invention the fifth step is cyclisation using iodine to give spiroiodo compounds.

In yet another embodiment of the present invention the sixth step is conversion of iodo to azide to give spiroazide compounds.

In still another embodiment of the present invention the seventh step is treatment of spiroazides with alkynes to give triazole based spirooxindoles.

In still another embodiment of the present invention the reaction of spiroiodo compounds with cyclic amines gives the cyclic amine based spirooxindoles.

In still another embodiment of the present invention the spirooxindole compounds prepared are tested for their efficiency towards GSK3β inhibition property and their anti-cancer potential.

DETAILED DESCRIPTION OF THE INVENTION

Figure 1:
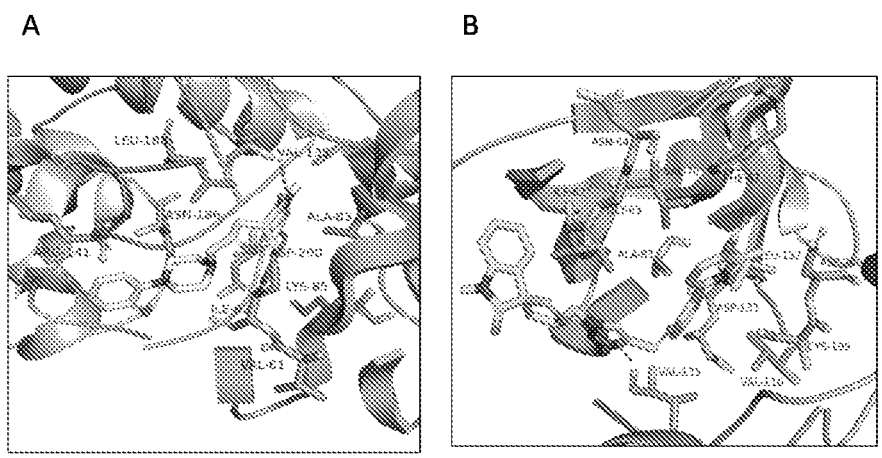
FIG. 1: Screening of GSK3β Inhibitors Using the ADP-Glo Kinase Assay.

Spirooxindoles are efficient structural motifs capable of showing diverse biological activities.

This resulted in design and synthesis of a large number of spirooxindoles as illustrated in Scheme 1, which comprises of:

The process for the preparation of spirooxindoles wherein the said process comprising the steps of:
a) allylation of oxindole
b) protection of free amine with boc group
c) formylation using formaldehyde
d) removal of the protection to give free amine
e) cyclisation using iodine to give spiro-iodo compounds
f) azidation of spiro-iodo compounds using sodium azide to give spiro-azide compounds or reaction of spiro-iodo compounds with cyclic amines to give the cyclic amine based spirooxindoles
g) reaction of spiro-azide compounds with alkynes to give triazole based spirooxindoles under click chemistry conditions.

EXAMPLES

The present invention will be more specifically explained by following examples. However, the scope of the present invention is not limited to the scope of the examples stated below.

Experimental Section

Example 1

3-Allylindolin-2-one (2)

To a stirred solution of oxindole (10 g, 75 mmol) in dry THF (200 mL) under inert condition was added tetra methyl ethylene diamine (TMEDA) (22.5 g, 150 mmol) and the resulting solution was cooled to −78° C. After 10 min, nBuLi (60 mL, 2.5 M in hexanes) was added slowly drop by drop over 30 min, and then allowed to stir for another 30 min. Then allyl bromide (16 g, 124.34 mmol) was added slowly to the reaction mixture, warmed to −23° C., and maintained for 4 h, after the completion of reaction (monitored by TLC) saturated $NH_4Cl$ (100 mL) was added and extracted with EtOAc (3×200 mL). The combined organic layers were washed with brine and dried over $Na_2SO_4$. The solvent was evaporated in vacuum and the residue was purified by column chromatography on silica gel eluting with hexanes/EtOAc (70:30) to give allyl oxindole (9.07 g, 70% yield).
$^1$H NMR (300 MHz, $CDCl_3$): δ 8.71 (br s, 1H), 7.27 (d, 1H, J=5.7 Hz), 7.21 (t, 1H, J=7.6 Hz), 7.02 (t, 1H, J=7.6 Hz), 7.02 (td, 1H, J=6.8 Hz), 6.90 (td, 1H, J=7.7 Hz), 5.77 (m, 1H), 5.18-5.04 (dd, 2H, J=10.0 Hz), 3.53 (q, 1H, J=5.0 Hz), 2.84 (m, 1H), 2.60 (m, 1H); $^{13}$C NMR (300 MHz, $CDCl_3$): δ 180.1, 141.2, 133.8, 129.2, 127.2, 124.3, 122.1, 118.0, 109.8, 45.7, 34.7; ESI-MS: m/z 174 [M+H]$^+$.

Example 2 tert-Butyl 3-allyl-2-oxoindoline-1-carboxylate (3)

To a stirred solution of allyl oxindole 2 (5 g, 28.9 mmol) in dry THF (50 mL), was added $Na_2CO_3$ (6.123 g, 57.08 mmol) at room temperature, after 5 min (Boc)$_2$O (6.9 g, 31.97 mmol) was added and then reaction mixture was heated to 60° C. The reaction was allowed to stir vigorously for 6 h under $N_2$-atmosphere. Then the reaction mixture was cooled to room temperature, diluted with water and extracted with EtOAc (2×100 mL). The combined organic layers were given a brine wash (20 mL) and dried over anhydrous $Na_2SO_4$. The solvent was concentrated in vacuo and the residue was purified by silica gel column using EtOAc/petroleum ether (5:95) to afford the Boc protected allyl oxindole compound 3 (6.39 g, 80% yield).
$^1$H NMR (300 MHz, $CDCl_3$): δ 7.80 (d, 1H, J=8.1 Hz), 7.34-7.25 (m, 2H), 7.14 (t, 1H, J=7.3 Hz), 5.83-5.67 (m, 1H), 5.18-5.01 (m, 2H), 3.61 (t, 1H, J=6.0 Hz), 2.89-2.77 (m, 1H), 2.71-2.51 (m, 1H), 1.64 (s, 9H); $^{13}$C NMR (75 MHz, $CDCl_3$): δ 175.5, 149.1, 133.4, 131.5, 130.8, 128.0, 124.1, 123.9, 118.5, 114.8, 84.2, 45.6, 35.4, 27.9; MASS (ESI): mi/z 296 [M+Na]$^+$.

Example 3 tert-Butyl 3-allyl-3-(hydroxymethyl)-2-oxoindoline-1-carboxylate (4)

To a stirred solution of Boc oxindole 3 (5.0 g, 18.30 mmol) in dry DME (30 mL) was added quinine (0.059 g, 0.183 mmol), followed by HCHO (0.82 g, 27.84 mmol) and the resulting mixture was stirred at room temperature for 20 h. After completion of the reaction (monitored by TLC), the reaction mixture was partitioned between water (20 mL) and EtOAc (50 mL). The organic layer was separated and the aqueous phase was extracted with EtOAc (2×40 mL) and the combined organic layers were washed with brine and dried over $Na_2SO_4$. The solvent was evaporated in vacuo and the residue was purified by column chromatography on silica gel eluted with hexanes/EtOAc (85:15) to give hydroxyl methyl compound 4 (5.43 g, 98% yield).
$^1$H NMR (300 MHz, $CDCl_3$): b 7.80 (d, 1H, J=8.1 Hz), 7.34-7.25 (m, 2H), 7.14 (t, 1H, J=7.3 Hz), 5.83-5.67 (m, 1H), 5.18-5.01 (m, 2H), 4.15-3.92 (m, 2H), 2.89-2.77 (m, 1H), 2.71-2.51 (m, 1H), 1.54 (s, 9H); $^{13}$C NMR (75 MHz, $CDCl_3$): δ 175.9, 151.5, 149.0, 135.4, 130.8, 128.0, 124.1, 123.9, 118.5, 114.8, 84.2, 79.2, 45.6, 35.4, 27.9; MASS (ESI): m/z 326 [M+Na]$^+$.

Example 4

3-Allyl-3-(hydroxymethyl) indolin-2-one (5)

To a solution of alcohol 4 (2.0 g, 6.60 mmol) in dichloromethane (30 mL) was added trifluoroacetic acid (1.52 g, 13.76 mmol) at 0° C. The reaction mixture was stirred at 0° C. for 1 h and another 6 h at room temperature. After completion of the reaction (monitored by TLC), the solvent and TFA was removed under reduced pressure below 45° C. The residue was diluted with $CH_2Cl_2$ (50 mL) and water (50 mL). The organic layer was separated, washed with brine (20 mL), the combined organic layer was dried over anhydrous $Na_2SO_4$ and concentrated in vacuo. The residue was purified by silica gel column chromatography using petroleum ether/EtOAc (75:25) to afford Boc deprotected compound 5 (1.07 g, 80% yield) as yellowish liquid.
$^1$H NMR (300 MHz, $CDCl_3$): δ 8.18 (s, 1H), 7.27 (m, 2H), 7.07 (m, 1H), 6.90 (d, J=2.7 Hz, 1H), 5.49 (m, 1H), 5.04 (m, 1H), 4.95 (dd, J=10.2 Hz, 1H), 3.92 (d, J=11.2 Hz, 1H), 3.80 (d, J=10.9 Hz, 1H), 2.64 (m, 2H), 1.72 (s, 1H); $^{13}$C NMR (75 MHz, $CDCl_3$): J 180.0, 141.5, 133.8, 129.1, 127.9, 124.3, 122.1, 118.0, 109.7, 66.4, 54.9, 37.2; ESI-MS: m/z 204 [M+H]$^+$; IR (Neat): 3437, 2982, 1789, 1730, 1609, 1152, 844, 771, 676 cm$^{-1}$.

General Procedure for Spiro-Iodo Compounds (6a and 6b)

To the solution alcohol 5 (2 g, 9.85 mmol) in acetonitrile (30 mL), were added iodine (5.52 g, 20.68 mmol) and $Na_2CO_3$ (2.19 g, 20.68 mmol), and the resulting reaction mixture was stirred for 12 h at reflux. After complete conversion of starting material (monitored by TLC), reaction was quenched with saturated hypo solution (20 mL), then stirred for another 15 min, and extracted with EtOAc (3×50 mL). Combined organic layers were washed with brine (50 mL), dried over anhydrous $Na_2SO_4$ and concentrated in vacuo. The residue was purified by silica gel column chromatography using petroleum ether/EtOAc (80:20) to afford spiro-iodo compounds

Example 5

5-(Iodomethyl)-4,5-dihydro-2H-spiro[furan-3,3'-indolin]-2'-one (6a)

Yield=78%; White solid; mp-170.6° C.; IR (neat): $v_{max}$ 3243, 2927, 1711, 1619, 1341, 1188, 1070, 752, 632 $cm^{-1}$; $^1H$ NMR (300 MHz, $CDCl_3$): δ 8.48 (br, s, 1H), 7.21-7.28 (m, 2H), 7.09 (t, J=7.5 Hz, 1H), 6.95 (d, J=8.3 Hz, 1H), 4.57-4.63 (m, 1H), 4.30 (d, J=8.3 Hz, 1H), 4.01 (d, J=8.3 Hz, 1H), 3.41-3.47 (m, 2H), 2.35-2.41 (m, 2H); $^{13}CNMR$ (75 MHz, $CDCl_3$): δ 180.2, 140.0, 133.3, 128.3, 123.0, 122.8, 110.2, 80.2, 76.3, 55.8, 44.1, 8.0; ESI-MS: m/z 352 [M+Na]+; HRMS: calcd for $C_{12}H_{12}IO_2NNa$ 352.1110 found 352.1252.

Example 6

5'-Iodo-2', 4', 5', 6'-tetrahydrospiro [indoline-3,3'-pyran]-2-one (6b)

3.17 g 78% yield); white solid.
$^1H$ NMR (300 MHz, $CDCl_3$): δ 7.39 (d, 1H, J=7.4 Hz), 7.27-7.21 (m, 2H), 7.08 (t, 1H, J=7.4 Hz), 6.93 (d, 1H), 4.39-4.32 (m, 1H), 4.16 (s, 2H), 3.52-3.42 (m, 2H), 2.63 (dd, 1H, J=6.4 Hz & 13.1 Hz), 2.04 (dd, 1H, J=9.0 Hz & 12.9 Hz); $^{13}C$ NMR (75 MHz, $CDCl_3$): δ 181.0, 140.2, 133.0, 128.3, 123.1, 123.1, 109.8, 79.1, 77.0, 55.2, 44.6, 8.3; MASS (ESI): m/z 252 [M+Na]+.

Example 7

5-(Azidomethyl)-4,5-dihydro-2H-spiro[furan-3,3'-indolin]-2'-one (7a)

To a solution of iodide 6a (2.5 g, 7.58 mmol) in dry DMF (15 mL) was added $NaN_3$ (0.74 g, 11.3 mmol) under inert condition and the resulting mixture was heated to 80° C. for 12 h. After completion of the reaction (monitored by TLC), reaction mixture was diluted with cool water (30 mL), and extracted with diethyl ether (2×75 mL). Organic layer was washed with cool water for two times and the layers are separated. The organic layer was washed with brine (20 mL), dried over anhydrous $Na_2SO_4$ and concentrated in vacuo. The crude azide obtained was purified by column chromatography on silica gel eluted with hexanes/EtOAc (80:20) to give spiro-azide 7a (2.0 g, 81% yield) as a pale yellow liquid.
Yield=81%; liquid; IR (neat): $v_{max}$ 3247, 2925, 2856, 2101, 1712, 1619, 1471, 1082, 752, 681 $cm^{-1}$; $^1H$ NMR (300 MHz, $CDCl_3$): δ 8.35 (br, s, 1H), 7.37 (d, J=7.5 Hz, H), 7.26 (t, J=7.5 Hz, 1H), 7.08 (t, J=7.5 Hz, 1H), 6.90 (d, J=6.9 Hz, 1H), 4.51-4.58 (m, 1H), 4.1 (s, 2H), 3.68 (dd, J=3.7 Hz, 1.2 Hz 1H), 3.42 (dd, J=5.2 Hz, 3.2 Hz, 1H), 2.52 (dd, 1=6.7 Hz, 5.1 Hz 1H), 2.12 (dd, J=9.8 Hz, 3.6 Hz, 1H); $^{13}C$ NMR (75 MHz, $CDCl_3$): δ 180.1, 141.1, 132.3, 128.3, 122.0, 121.8, 111.1, 80.2, 75.3, 56.8, 55.1, 37.2; ESI-MS: m/z 245 [M+H]+; HRMS: calcd for $C_{12}H_{12}O_2N_4Na$ 247.1210 found 247.1252.

Example 8

5'-Azido-2',4',5',6'-tetrahydrospiro[indoline-3,3'-pyran]-2-one (7b)

To a solution of iodide 6b (2.5 g, 7.58 mmol) in dry DMF (15 mL) was added $NaN_3$ (0.74 g, 11.3 mmol) under inert condition and the resulting mixture was heated to 80° C. for 12 h. After completion of the reaction (monitored by TLC), reaction mixture was diluted with cool water (30 mL), and extracted with diethyl ether (2×75 mL). Organic layer was washed with cool water for two times and the layers are separated. The organic layer was washed with brine (20 mL), dried over anhydrous $Na_2SO_4$ and concentrated in vacuo. The crude azide obtained was purified by column chromatography on silica gel eluted with hexanes/EtOAc (80:20) to give spiro-azide 7b (2.0 g, 81% yield) as a pale yellow liquid.
$^1H$ NMR (300 MHz, $CDCl_3$): δ 9.28 (br, s, 1H), 7.35 (d, 1H, J=7.3 Hz), 7.24 (td, 1H, J=7.7 Hz, 1.2 Hz), 7.09 (td, 1H, J=7.6 Hz, 0.9 Hz), 6.95 (d, 1H, J=7.7 Hz), 4.58-4.53 (m, 1H), 4.11 (s, 2H), 3.67 (dd, 1H, J=12.9 Hz, 3.6 Hz), 3.46 (dd, 1H, J=13.1 Hz, 5.3 Hz), 2.51 (dd, 1H, J=12.8 Hz & 6.7 Hz), 2.12 (dd, 1H, J=12.9 Hz, 3.6 Hz); $^{13}C$ NMR (75 MHz, $CDCl_3$): δ 180.0, 140.0, 133.3, 128.3, 123.0, 122.8, 110.2, 79.1, 76.1, 55.2, 53.8, 41.0; MASS (ESI): m/z 267 [M+Na]+.
General Procedure for Spirooxindole-Triazoles (9a and 9b)
Spiro-azide 7a/7b (0.5 mmol), terminal alkyne (0.5 mmol), dry $Et_3N$ (1.0 mmol), THF (6 mL) and dry CuI (0.5 mmol) were added successively under $N_2$ atmosphere. Reaction mixture was stirred for 2 h at room temperature, and then water (3 mL) was added, crude was extracted with EtOAc (3×15 mL). The combined organic layers were washed with brine solution and dried over $Na_2SO_4$. The solvent was evaporated in vacuo and the residue was purified by column chromatography to afford triazole (9a and 9b).

Example 9

Ethyl 6-(5-fluoro-2-((1-(2-oxo-2', 4', 5', 6'-tetrahydrospiro[indoline-3,3'-pyran]-5'-yl)-1H-1,2,3-triazol-4-yl)methoxy)-phenyl)-2-methylnicotinate (AC-A)

$^1H$ NMR (300 MHz, $CDCl_3$): δ 8.17 (d, 1H, J=8.2 Hz), 7.90 (d, 1H, J=8.2 Hz), 7.68 (dd, 1H, J=3.2 Hz & 9.4 Hz), 7.57 (br, 1H), 7.28-7.23 (m, 2H), 7.22-7.18 (m, 1H), 7.11-7.05 (m, 2H), 6.90 (d, 1H, J=7.6 Hz), 5.19-5.11 (m, 2H), 4.96-4.90 (m, 1H), 4.77-4.71 (m, 1H), 4.63-4.58 (m, 1H), 4.39-4.32 (q, 2H, J=7.0 Hz), 4.27 (d, 1H, J=8.8 Hz), 3.95 (d, 11H, J=8.8 Hz), 2.88 (s, 3H), 2.47-2.36 (m, 2H), 1.39 (t, 3H, J=7.1 Hz); $^{13}C$ NMR (75 MHz, $CDCl_3$): δ 179.4, 166.3, 159.7, 155.4, 150.9, 142.9, 139.9, 138.9, 136.6, 132.6, 131.7, 130.3, 129.8, 128.5, 124.3, 124.5, 123.2, 123.0, 121.9, 109.9, 78.8, 76.3, 66.9, 61.3, 54.7, 53.2, 41.1, 25.0, 14.2; MASS (ESI): m/z 580 [M+Na]+.

Example 10

Ethyl 2-methyl-6-(2-((1-(2-oxo-2',4',5',6'-tetrahydrospiro[indoline-3,3'-pyran]-5'-yl)-1H-1,2,3-triazol-4-yl)methoxy)-phenyl)nicotinate (AC-B)

$^1H$ NMR (300 MHz, $CDCl_3$): b 8.11 (d, 1H, J=8.2 Hz), 8.06 (br, 5H), 7.84 (dd, 1H, J=1.6 Hz, 7.6 Hz), 7.79 (s, 1H), 7.77 (d, 1H, J=8.2 Hz), 7.73-7.70 (m, 0.5H), 7.55-7.52 (m, 0.5H), 7.42-7.38 (m, 1H), 7.19-7.11 (m, 3H), 6.89 (dt, 1H,

J=0.9 Hz & 7.6 Hz), 6.84 (d, 1H, J=7.7 Hz), 6.80 (d, 1H, J=7.3 Hz), 5.34 (dd, 2H, J=12.2 Hz & 17.0 Hz), 4.77-4.66 (m, 2H), 4.61 (dd, 1H, J=5.1 Hz & 14.0 Hz), 4.34 (q, 2H, J=7.0 Hz), 4.05 (d, 1H, J=8.8 Hz), 3.89 (d, 1H, J=8.8 Hz), 2.88 (s, 3H), 2.53 (dd, 1H, J=6.4 Hz & 13.1 Hz), 1.91 (dd, 1H, J=9.6 Hz, 13.1 Hz), 1.36 (t, 3H, J=7.0 Hz); $^{13}$C NMR (75 MHz, CDCl$_3$): δ 180.3, 166.7, 159.4, 157.8, 155.8, 144.2, 140.0, 138.0, 132.1, 130.5, 128.9, 128.4, 124.2, 123.2, 122.5, 122.1, 121.8, 113.1, 109.6, 78.2, 77.1, 76.8, 62.8, 61.0, 52.4, 40.4, 29.6, 25.0, 14.2; MASS (ESI): m/z 539 [M+Na]$^+$.

Example 11

Ethyl 6-(5-chloro-2-((1-(2-oxo-2',4',5',6'-tetrahydrospiro [indoline-3,3'-pyran]-5'-yl)-1H-1,2,3-triazol-4-yl)methoxy)-phenyl)-2-methyl nicotinate (AC-C)

$^1$H NMR (300 MHz, CDCl$_3$): δ 8.25 (d, 1H, J=8.2 Hz), 7.85 (d, 1H, J=8.2 Hz), 7.78 (dd, 1H, J=3.2 Hz & 9.4 Hz), 7.69 (br, 1H), 7.5 (s, 2H), 7.28-7.21 (m, 1H), 7.09-7.05 (m, 2H), 6.95-6.91 (d, 1H, J=7.6 Hz), 4.95 (s, 2H), 4.73-4.68 (m, 1H), 4.62-4.57 (m, 1H), 4.43-4.39 (m, 1H), 4.26-4.24 (q, 2H, J=7.0 Hz), 3.95 (d, 1H, J=8.8 Hz), 2.88 (s, 3H), 2.37-2.36 (m, 2H), 1.39 (t, 3H, J=7.1 Hz); $^{13}$C NMR (75 MHz, CDCl$_3$): δ 179.4, 166.3, 159.7, 155.4, 150.9, 142.9, 138.9, 139.9, 136.0, 132.5, 130.7, 130.3, 129.8, 128.5, 124.5, 124.5, 123.2, 123.0, 121.9, 78.8, 76.3, 66.9, 61.3, 54.7, 53.2, 41.1, 25.0, 14.2; MASS (ESI): m/z 597 [M+Na]$^+$.

Example 12

Ethyl 6-(3,5-dichloro-2-((1-(2-oxo-2',4',5',6'-tetrahydrospiro-[indoline-3,3'-pyran]-5'-yl)-1H-1,2,3-triazol-4-yl)methoxy)phenyl)-2-methyl nicotinate (AC-D)

$^1$H NMR (300 MHz, CDCl$_3$): δ 8.26 (d, 1H, J=8.0 Hz), 7.82 (d, 1H, J=8.0 Hz), 7.76 (dd, 1H, J=0.9 Hz & 2.8 Hz), 7.67 (s, 1H), 7.48 (dd, 1H, J=0.9 Hz & 2.5 Hz), 7.28-7.23 (m, 3H), 7.08 (t, 1H, J=7.4 Hz), 6.93 (d, 1H, J=8.5 Hz), 4.97 (s, 2H), 4.76-4.67 (m, 2H), 4.60-4.55 (m, 1H), 4.39 (q, 2H, J=7.6 Hz), 4.25 (d, 1H, J=8.8 Hz), 3.96 (d, 1H, J=8.8 Hz), 2.90 (s, 3H), 2.38-2.26 (m, 2H), 1.41 (t, 3H, J=7.6 Hz); $^{13}$C NMR (75 MHz, CDCl$_3$): δ 178.5, 166.8, 159.5, 155.7, 151.8, 142.9, 139.7, 138.9, 136.2, 132.5, 130.7, 130.4, 129.8, 128.5, 124.5, 124.5, 123.3, 123.0, 121.9, 109.9, 78.8, 76.3, 66.9, 61.5, 54.7, 53.2, 41.1, 25.1, 14.1; MASS (ESI): m/z 631 [M+Na]$^+$.

Example 13

2-((1-(2-oxo-2', 4', 5', 6'-tetrahydrospiro[indoline-3, 3'-pyran]-5'-yl)-1H-1,2,3-triazol-4-yl) methoxy)benzaldehyde (AC-E)

$^1$H NMR (300 MHz, CDCl$_3$): δ 10.49 (s, 1H), 7.92 (s, 1H), 7.85 (dd, 1H, J=1.6 Hz & 7.6 Hz), 7.63 (br, 1H), 7.59-7.55 (m, 1H), 7.28-7.23 (m, 1H), 7.20 (d, 1H, J=8.3 Hz), 7.07 (q, 2H, J=7.3 Hz), 6.91 (d, 1H, J=7.6 Hz), 5.37 (s, 2H), 4.79-4.74 (m, 1H), 4.69-4.63 (m, 1H), 4.25 (d, 1H, J=8.8 Hz), 3.96 (d, 1H, J=8.8 Hz), 2.96 (s, 0.5H), 2.89 (s, 0.5H), 2.40-2.34 (m, 1H), 2.33-2.27 (m, 1H); $^{13}$C NMR (75 MHz, CDCl$_3$): δ 190.0, 182.3, 162.2, 142.1, 140.9, 139.8, 135.0, 131.2, 126.5, 125.5, 124.8, 123.1, 122.7, 122.6, 114.5, 110.2, 75.4, 73.2 71.0, 56.6, 51.1, 32.4; IR: 2959, 2870, 1720, 1691, 772 cm$^{-1}$; MASS (ESI): m/z 427 [M+Na]$^+$.

Example 14

5'-(4-(Pyridin-2-yl)-1H-1,2,3-triazol-1-yl)-2',4',5',6'-tetrahydrospiro[indoline-3,3'-pyran]-2-one (AC-F)

$^1$H NMR (300 MHz, CDCl$_3$): δ 10.18 (br, 1H), 8.59 (br, 1H), 8.41 (s, 1H), 8.13 (d, 1H, J=7.7 Hz), 7.80 (t, 1H, J=7.5 Hz), 7.33-7.15 (m, 3H), 7.0 (t, 1H, J=7.5 Hz), 6.91 (d, 1H, J=7.7 Hz), 4.90-4.70 (m, 3H), 4.23 (d, 1H, J=8.6 Hz), 3.94 (d, 1H, J=8.6 Hz), 2.42-2.30 (m, 2H); $^{13}$C NMR (75 MHz, CDCl$_3$): δ 178.2, 159.1, 148.7, 140.6, 136.2, 132.3, 127.6, 122.7, 122.1, 122.0, 122.0, 121.8, 119.4, 109.4, 78.0, 75.7, 54.2, 52.8, 40.4; IR: 3017, 2871, 1712, 1601, 1217, 771 cm$^{-1}$; MASS (ESI): m/z 370 [M+Na]$^+$.

Example 15

5'-(4-(Hydroxy(phenyl)methyl)-1H-1,2,3-triazol-1-yl)-2',4',5',6'-tetrahydrospiro[indoline-3,3'-pyran]-2-one (AC-G)

$^1$H NMR (300 MHz, CDCl$_3$): δ 8.10 (d, 1H, J=7.1 Hz), 7.93 (br, 1H), 7.88-7.80 (m, 1H), 7.68-7.30 (m, 3H), 7.07 (t, 1H, J=7.7 Hz), 6.90 (d, 1H, J=6.7 Hz), 4.99-4.52 (m, 3H), 4.31-4.08 (m, 1H), 3.99-3.88 (m, 1H), 2.50-2.19 (m, 2H); $^{13}$C NMR (75 MHz, CDCl$_3$): δ 179.8, 139.9, 133.2, 130.5, 130.0, 128.9, 128.6, 128.6, 128.5, 128.3, 126.5, 123.2, 122.9, 110.1, 78.7, 76.3, 64.2, 54.7, 53.4, 29.6; IR: 3019, 1710, 1214, 745 cm$^{-1}$; MASS (ESI): m/z 399 [M+Na]$^+$.

Example 16

5'-(4-((2-Nitrophenoxy)methyl)-1H-1,2,3-triazol-1-yl)-2',4',5',6'-tetrahydrospiro-[indoline-3,3'-pyran]-2-one (AC-H)

$^1$H NMR (300 MHz, CDCl$_3$): δ 8.18-8.14 (m, 1H), 7.85-7.92 (m, 1H), 7.61-7.55 (m, 1H), 7.58-7.51 (m, 1H), 7.17-7.05 (m, 2H), 6.94-6.90 (m, 1H), 6.80-6.72 (m, 2H), 6.02-5.98 (m, 1H), 4.80-4.67 (m, 3H), 4.27-4.21 (m, 3H), 4.18-4.10 (m, 1H), 3.98-3.90 (m, 1H), 3.51-3.47 (m, 1H), 2.39-2.32 (m, 2H); $^{13}$C NMR (75 MHz, CDCl$_3$): δ 180.1, 155.4, 144.6, 143.3, 142.8, 140.2, 129.3, 127.8, 126.5, 123.1, 122.1, 114.5109.5, 104.6, 99.6, 78.2, 75.7, 54.2, 53.4, 52.0, 35.4; MASS (ESI): m/z 444 [M+Na]$^+$.

Example 17

5'-(4-((4-Chloro-2-methylphenoxy)methyl)-1H-1,2, 3-triazol-1-yl)-2',4',5',6'-tetra hydrospiro[indoline-3, 3'-pyran]-2-one (AC-I)

$^1$H NMR (300 MHz, CDCl$_3$): δ 8.80 (br, 1H), 7.85 (s, 1H), 7.77-7.56 (m, 1H), 7.36-7.19 (m, 2H), 7.13-6.85 (m, 3H), 5.19 (s, 2H), 4.82-4.60 (m, 3H), 4.22 (d, 1H, J=8.6 Hz), 3.94 (d, 1H, J=8.6 Hz), 2.47-2.40 (br, 1H), 2.37-2.28 (m, 1H), 2.19 (s, 3H); $^{13}$C NMR (75 MHz, CDCl$_3$): δ 179.7, 154.8, 144.0, 132.4, 130.4, 129.7, 128.5, 128.2, 128.0, 126.3, 123.9, 123.1, 122.8, 112.6, 110.0, 78.7, 76.3, 62.2, 54.7, 53.3, 40.9, 16.1; MASS (ESI): m/z 447 [M+Na]+.

Example 18

5'-(4-((3-Hydroxyphenylamino)methyl)-1H-1,2,3-triazol-1-yl)-2',4',5',6'-tetrahydrospiro[indoline-3,3'-pyran]-2-one (AC-J)

$^1$H NMR (300 MHz, CDCl$_3$): δ 9.57 (br, 1H), 8.13 (br, 1H), 7.77-7.72 (m, 1H), 7.36-7.31 (m, 1H), 7.27-7.19 (m, 2H), 7.07-6.96 (m, 2H), 6.95-6.90 (m, 1H), 6.27-6.19 (m, 2H), 4.79-4.60 (m, 3H), 4.49-4.26 (m, 3H), 4.21-4.14 (m, 1H), 3.94-3.88 (m, 11H), 2.30-2.23 (m, 1H), 2.22-2.16 (m, 2H); $^{13}$C NMR (75 MHz, CDCl$_3$): δ 180.1, 158.5, 148.7, 146.5, 143.3, 129.3, 128.5, 126.8, 122.5, 122.1, 122.3, 109.5, 107.7, 106.6, 99.6, 77.2, 75.7, 55.2, 51.8, 42.3, 35.4; IR: 3476, 2922, 1733, 1232, 1018, 749 cm$^{-1}$; MASS (ESI): m/z 414 [M+Na]+.

Example 19

5'-(4-((3-Aminophenoxy)methyl)-1H-1,2,3-triazol-1-yl)-2',4',5',6'-tetrahydrospiro[indoline-3,3'-pyran]-2-one (AC-K)

$^1$H NMR (300 MHz, CDCl$_3$): δ 12.12-12.08 (m, 1H), 8.08 (brs, 1H), 7.98-7.92 (m, 1H), 7.91-7.85 (m, 1H), 7.58-7.51 (m, 1H), 7.17-7.05 (m, 2H), 6.95-6.90 (m, 1H), 6.80-6.72 (m, 2H), 6.02-5.98 (m, 1H), 4.80-4.65 (m, 3H), 4.27-4.20 (m, 3H), 4.18-4.10 (m, 1H), 3.98-3.90 (m, 1H), 3.51-3.47 (m, 1H), 2.39-2.30 (m, 2H); $^{13}$C NMR (75 MHz, CDCl$_3$): δ 179.0, 157.4, 148.6, 146.3, 145.8, 140.2, 129.3, 127.8, 122.5, 122.1, 122.1, 109.5, 104.7, 104.6, 99.6, 78.2, 75.7, 54.2, 52.4, 52.3, 40.0; MASS (ESI): m/z 414 [M+Na]−.

Example 20

5'-(4-((5-Bromo-3-nitropyridin-2-yloxy)methyl)-1H-1,2,3-triazol-1-yl)-2',4',5',6'-tetrahydro spiro[indoline-3,3'-pyran]-2-one (AC-L)

$^1$H NMR (300 MHz, CDCl$_3$): δ 8.41 (d, 1H, J=2.4 Hz), 8.27 (d, 1H, J=2.4 Hz), 8.15 (s, 1H), 7.29-7.20 (m, 3H), 7.06 (t, 1H, J=7.5 Hz), 6.97-6.90 (m, 1H), 5.44-5.23 (m, 2H), 4.81-4.64 (m, 3H), 4.23 (d, 1H, J=8.6 Hz), 3.95 (d, 1H, J=8.8 Hz), 2.41-2.22 (m, 2H); $^{13}$C NMR (75 MHz, CDCl$_3$): δ 180.1, 155.8, 154.7, 140.3, 138.7, 135.8, 130.6, 125.2, 124.1, 122.0, 121.8, 110.2, 101.9, 74.4, 73.5, 71.5, 56.2, 51.8, 30.8; MASS (ESI): m/z 524 [M+Na]+.

Example 21

Ethyl 2-methyl-6-(2-((1-((2'-oxo-4,5-dihydro-2H-spiro[furan-3,3'-indoline]-5-yl)methyl)-1H-1,2,3-triazol-4-yl)methoxy)phenyl)nicotinate (AB-0)

Yield=72%; Semi solid; IR (neat): ν$_{max}$ 3206, 2929, 1716, 1584, 1265, 1010, 771 cm$^{-1}$; $^1$H NMR (300 MHz, CDCl$_3$): δ 8.52 (s, 1H), 8.25 (dd, J=8.1 Hz, 3.7 Hz, 1H,), 7.84-7.93 (m, 3H), 7.46-7.31 (m, 4H), 6.80-6.86 (m, 2H), 5.39 (d, J=9.0 Hz, 4.7 Hz, 1H), 4.57-4.63 (m, 3H), 4.31-4.37 (m, 2H), 4.16 (dd, J=7.1 Hz, 6.7 Hz, 1H), 3.91 (dd, J=8.8 Hz, 3.7 Hz, 1H), 2.87 (d, J=4.3 Hz, 3H), 2.51 (d, J=4.3 Hz, 3H), 2.51-2.34 (m, 1H), 1.34-1.41 (m, 3H); $^{13}$CNMR (75 MHz, CDCl$_3$): δ 180.0, 166.6, 159.3, 157.7, 144.2, 138.0, 132.5, 132.0, 131.4, 130.5, 128.6, 128.7, 128.4, 128.0, 123.9, 122.8, 122.3, 113.0, 110.2, 109.8, 78.7, 78.1, 62.4, 61.1, 64.4, 52.5, 40.3, 25.0, 14.1; MS (ESI): m/z 540 [M+H]+; HRMS [M+H]+: calcd for C$_{30}$H$_{30}$O$_5$N$_5$ 540.2202, found 540.2241.

Example 22

Ethyl 6-(5-fluoro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate (AB-M)

Yield=77%; Semi solid; IR (neat): ν$_{max}$ 3215, 2930, 1717, 1472, 1261, 771, 680 cm$^{-1}$; $^1$H NMR (300 MHz, CDCl$_3$): δ 8.31 (s, 1H), 7.79-7.85 (m, 3H), 7.25-7.02 (m, 5H), 6.91-6.84 (m, 2H), 5.42-5.49 (m, 2H), 4.81-4.89 (m, 3H), 4.52-3.92 (m, 4H), 2.87 (s, 3H), 2.54 (dd, J=6.5 Hz, 4.7 Hz, 1H), 2.34 (dd, J=7.6 Hz, 3.7 Hz, 1H), 1.37 (t, J=7.1 Hz, 3H); $^{13}$CNMR (75 MHz, CDCl$_3$): δ 180.8, 166.5, 159.4, 156.2, 152.0, 143.4, 140.3, 138.3, 132.0, 130.1, 129.1, 128.1, 124.5, 123.3, 122.9, 122.0, 117.0, 116.1, 114.4, 109.1, 78.5, 78.1, 63.3, 61.0, 54.4, 52.4, 40.1, 29.1, 24.1, 13.1; ESI-MS: m/z 558[M+H]+; HRMS[M+H]+: calcd for C$_{30}$H$_{28}$O$_5$N$_5$FNa 580.1932, found 580.1932.

Example 23

Methyl-6-(5-chloro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate (AB-N)

Yield=71%; Solid; mp: 120-122° C.; IR (neat): ν$_{max}$ 3218, 2926, 1718, 1619, 1557, 1263, 771, 678 cm$^{-1}$; $^1$H NMR (300 MHz, CDCl$_3$): δ 8.13 (d, 1=8.2 Hz, 1H), 7.83-7.63 (m, 1H), 7.25-7.02 (m, 4H), 6.91 (dd, J=8.0 Hz, 3.7 Hz, 1H), 6.81-6.89 (m, 1H), 5.29 (d, J=8.0 Hz, 2H), 4.78-4.54 (m, 3H), 4.32-4.38 (m, 2H), 4.12-3.92 (m, 3H), 2.87 (s, 3H), 2.52-2.34 (m, 2H), 1.37 (s, 3H); $^{13}$CNMR (75 MHz, CDCl$_3$): δ 180.8, 166.5, 159.4, 156.2, 152.0, 143.4, 140.3, 138.3, 5132.0, 130.1, 129.4, 128.1, 124.5, 122.9, 122.0, 117.0, 116.1, 114.4, 109.1, 123.3, 78.5, 78.1, 63.3, 61.0, 54.4, 52.4, 40.1, 29.1, 13.2; ESI-MS: m/z 560 [M+H]+; HRMS: calcd for C$_{29}$H$_{27}$O$_5$N$_5$Cl 560.1657, found 560.1692.

Example 24

2-((1-((2'-Oxo-4,5-dihydro-2H-spiro[furan-3,3'-indoline]-5-yl)methyl)-1H-1,2,3-triazol-4-yl)methoxy)benzaldehyde (AB-P)

Yield=71%; Semi solid; IR (neat): ν$_{max}$ 2930, 2868, 1714, 1689, 1599, 1471, 1236, 1005, 754, 680 cm$^{-1}$; $^1$H NMR (300 MHz, CDCl$_3$): δ 10.52 (s, 11H), 8.53 (s, 1H), 7.91 (s, 1H), 7.86 (dd, J=7.5 Hz, 6.7 Hz, 2H), 7.55-7.62 (m 1H), 7.30-6.85 (m, 3H), 5.40 (s, 2H), 4.84-4.62 (m, 4H), 4.17-3.96 (m, 3H), 2.58 (dd, J=6.8 Hz, 2.7 Hz, 1H), 1.95 (dd, J=6.1 Hz, 4.7 Hz, 1H); $^{13}$CNMR (75 MHz, CDCl$_3$): δ 189.6, 189.5, 160.5, 143.4, 136.0, 136.0, 128.5, 128.7, 124.6, 123.1, 122.4, 121.3, 113.0, 110.0, 78.1, 76.6, 62.4, 54.3, 52.8, 40.6, 29.7; ESIMS: m/z 427 [M+Na]+; HRMS: calcd for C$_{22}$H$_{20}$O$_4$N$_4$Na 427.1349, found 427.1376.

Example 25

Ethyl6-(3,5-dichloro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate (AB-W)

Yield=78%; Solid; mp: 132-135° C.; IR (neat): $v_{max}$ 3197, 2925, 1719, 1712, 1620, 1468, 1078, 965, 754, 680 cm$^{-1}$; $^1$H NMR (300 MHz, CDCl$_3$): δ 8.81 (s, 1H), 8.23 (d, J=8.1 Hz, 1H), 7.81 (d, J=8.1 Hz, 1H), 7.77 (dd, J=5.65 Hz, 2.6 Hz, 2H), 7.44-7.49 (n, 1H), 7.26-6.86 (m, 5H), 5.0 (d, J=7.5 Hz, 2H), 4.76-4.58 (m, 2H), 4.40-4.42 (m, 2H), 4.18-4.25 (m, 2H), 3.85-3.91 (m, 1H), 2.89 (d, J=3.02 Hz, 2H), 2.52-2.58 (m 1H), 2.28-2.33 (m, 1H), 1.37 (s, 3H); $^{13}$CNMR (75 MHz, CDCl$_3$): δ 180.8, 179.7, 166.3, 159.6, 155.4, 151.0, 143.1, 140.3, 138.9, 136.4, 132.5, 130.7, 130.3, 129.7, 128.4, 124.7, 123.0, 122.5, 121.8, 109.8, 78.8, 78.26, 67.2, 61.2, 60.3, 54.5, 52.4, 40.5, 24.9, 14.2; ESIMS: m/z 608 [M+H]+; HRMS: calcd for C$_{30}$H$_{27}$O$_5$N$_5$Cl$_2$Na 630.1249, found 630.1281.

Example 26

Ethyl-1-((2'-oxo-4,5-dihydro-2H-spiro[furan-3,3'-indoline]-5-yl)methyl)-1H-1,2,3-triazole-4-carboxylate (AB-F)

Yield=88%; White solid; mp: 133-134° C.; IR (neat): $v_{max}$ 3138, 2926, 2855, 1737, 1685, 1607, 1250, 1041, 7 54 cm$^{-1}$; $^1$H NMR (300 MHz, CDCl$_3$): δ 8.40 (s, 1H), 7.96 (dd, J=4.5 Hz, 5.2 Hz, 2H), 7.40-7.18 (m, 3H), 7.0-7.16 (m, 2H), 4.90-4.63 (m, 3H), 4.43-4.49 (m, 2H), 4.18-4.25 (m, 1H), 3.94-4.01 (m, 1H), 2.57-2.62 (m, 1H), 1.97-2.04 (m, 1H), 1.31-1.36 (m, 3H); $^{13}$CNMR (75 MHz, CDCl$_3$): δ 178.1, 167.4, 133.2, 129.0, 128.7, 125.4, 122.9, 123.3, 110.2, 107.1, 78.7, 78.0, 61.4, 60.6, 52.0, 41.4, 14.3; ESIMS: m/z 365 [M+Na]+; HRMS: calcd for C$_{17}$H$_{20}$N$_4$O$_4$Na 365.1632, found 365.1642.

Example 27

5-((4-Phenyl-1H-1,2,3-triazol-1-yl)methyl)-4,5-dihydro-2H-spiro[furan-3,3'-indolin]-2'-one (AB-C)

Yield=78%; White solid; mp: 175-177° C.; IR (neat): $v_{max}$ 3229, 2925, 2855, 1713, 1620, 1470, 1221, 1077, 769, 694 cm$^{-1}$; $^1$H NMR (300 MHz, DMSO): δ 9.22 (s, 1H), 7.28 (d, J=7.1 Hz, 1H), 7.02 (d, J=7.17 Hz, 2H), 7.01-7.09 (m, 3H), 6.29 (dd, J=7.3 Hz, 1H), 6.02-6.09 (m, 3H), 3.94-4.01 (m, 3H), 3.22 (dd, J=8.7 Hz, 3.8 Hz, 1H) 3.12 (dd, J=8.8 Hz, 1.9 Hz, 1H), 1.72 (dd, J=6.2 Hz, 1.9 Hz, 1H), 1.18 (dd, J=8.12 Hz, 3.9 Hz 1H); $^{13}$CNMR (300 MHz, DMSO): δ 179.4, 146.4, 140.6, 131.2, 129.7, 128.1, 127.8, 127.3, 127.2, 127.1, 127.6, 120.4, 120.0, 108.9, 77.4, 75.8, 66.2, 53.4, 51.8, 39.7; ESI-MS: m/z 347 [M+H]+; HRMS: calcd for C$_{20}$H$_{18}$O$_2$N$_4$Na 369.1325, found 369.1325.

Example 28

5-((4-(Hydroxymethyl)-1H-1,2,3-triazol-1-yl)methyl)-4,5-dihydro-2H-spiro[furan-3,3'-indolin]-2'-one (AB-G)

Yield=78%; Yellow liquid; IR (neat): $v_{max}$ 3352, 2956, 2922, 2852, 1712, 1468, 1220, 772 cm$^{-1}$; $^1$H NMR (300 MHz, CDCl$_3$): δ 9.94 (s, 1H), 7.84 (d, J=8.1 Hz, 1H), 7.20-6.83 (m, 4H), 4.80-4.58 (m, 5H), 3.93-3.98 (m, 2H), 3.08 (br, s, 1H), 2.47-2.53 (m, 1H), 2.20-2.28 (m, 1H); $^{13}$CNMR (75 MHz, CDCl$_3$): δ 181.2, 141.6, 131.9, 127.4, 124.0, 123.4, 121.9, 111.1, 78.2, 75.5, 68.3, 54.6, 52.2, 40.4, 36.5; ESI-MS: m/z 323 [M+Na]+; HRMS: calcd for C$_{15}$H$_{16}$O$_3$N$_4$Na 323.1114, found 323.1114.

Example 29

5-((4-(2-Hydroxypropan-2-yl)-1H-1,2,3-triazol-1-yl)methyl)-4,5-dihydro-2H-spiro[furan-3,3'-indolin]-2'-one (AB-E)

Yield=78%; Thick liquid; IR (neat): $v_{max}$ 3272, 2972, 2927, 1711, 1620, 1221, 760,680 cm$^{-1}$; $^1$HNMR (300 MHz, CDCl$_3$): δ 10.06 (s, 1H), 7.76 (d, J=13.2 Hz, 1H), 7.48 (s, 1H), 7.17-7.24 (m, 1H), 6.91-6.89 (m, 2H), 4.80-4.60 (m, 3H), 4.18-3.90 (m, 2H), 2.53 (dd, J=6.7 Hz, 4.2 Hz, 2H), 2.22-2.28 (m, 1H), 1.62 (d, J=13.5 Hz, 6H); $^{13}$CNMR (75 MHz, CDCl$_3$): δ 182.2, 155.9, 140.6, 130.9, 128.4, 125.1, 123.0, 122.4, 110.1, 77.5, 76.3, 68.3, 54.6, 52.2, 40.4, 30.5, 30.4; ESI-MS: m/z 351 [M+Na]+; HRMS: calcd for C$_{17}$H$_{21}$O$_3$N$_4$ 329.1604, found 329.1608.

Example 30

5-((4-(4-Nitrophenyl)-1H-1,2,3-triazol-1-yl)methyl)-4,5-dihydro-2H-spiro[furan-3,3'-indolin]-2'-one (AB-D)

Yield=70%; Thick liquid; IR (neat): $v_{max}$ 3272, 2926, 2855, 1715, 1655, 1517, 1338, 854, 680 cm$^{-1}$; $^1$HNMR (300 MHz, CDCl$_3$): δ 8.62 (s, 1H), 8.51-8.58 (m, 5H), 7.34-7.41 (m, 2H), 7.22-7.28 (m, 2H), 4.79-4.84 (m, 2H), 4.50-4.56 (m, 3H), 2.47-2.52 (m, 2H); $^{13}$CNMR (75 MHz, CDCl$_3$): δ 181.2, 162.6, 160.8, 140.3, 138.1, 134.5, 129.2, 129.2, 122.8, 115.3, 115.1, 77.9, 77.2, 74.3, 54.3, 53.8, 52.2, 51.8, 51.4, 42.4; ESIMS: m/z 392 [M+H]+; HRMS: calcd for C$_{20}$H$_{17}$O$_4$N$_5$Na 414.175, found 414.1759.

General Procedure for Spirooxindole-Amines (8)

To the spiro-iodo compound 6a (0.5 mmol) in Dry DMF was added secondary amine (0.5 mmol) and dry K$_2$CO$_3$ (0.6 mmol), under inert conditions, at room temperature and stirred for 15 min. Then the reaction mixture was heated to 80° C. and maintained with vigorous stirring for about 12 h, after completion of the reaction (monitored by TLC), solvent was evaporated in vacuum and the residue was purified by column chromatography with hexane/EtOAc (3:7) to elute product 8.

Example 31

5-((4-Phenylpiperazin-1-yl)methyl)-4,5-dihydro-2H-spiro[furan-3,3'-indolin]-2'-one (AB-X)

Yield=78%; Solid; mp: 130-132° C.; IR (neat): $v_{max}$ 3738, 2924, 2824, 1713, 1599, 1467, 1233, 1011, 755, 621 cm$^{-1}$; $^1$H NMR (300 MHz, CDCl$_3$): δ 8.57 (s, 1H), 7.27-7.34 (m, 5H), 7.04-7.14 (m, 4H), 4.25-3.94 (m, 4H), 3.22-3.28 (m, 3H), 2.78-2.85 (m, 4H), 2.58-2.68 (m, 2H), 2.11-2.18 (m, 2H); $^{13}$CNMR (75 MHz, CDCl$_3$): δ 180.3, 160.7, 151.8, 140.2, 130.7, 129.0, 128.1, 123.0, 122.9, 119.7, 117.0, 116.0, 109.9, 78.4, 70.2, 62.3, 62.3, 54.7, 53.7, 48.9, 42.9, 40.7; ESIMS: m/z 364 [M+H]+; HRMS: calcd for C$_{22}$H$_{26}$O$_2$N$_3$ 364.2016, found 364.2019.

Example 32

5-(Morpholinomethyl)-4, 5-dihydro-2H-spiro[furan-3, 3'-indolin]-2'-one (AB-K)

Yield=83%; white solid; mp: 126-128° C.; IR (neat): $v_{max}$ 3225, 2925, 1715, 1470, 1219, 772, 626 cm$^{-1}$; $^1$H NMR (300 MHz, CDCl$_3$): δ 8.2 (s, 1H), 7.32 (d, J=7.5 Hz, 1H), 7.24 (t, J=7.3 Hz, 2H), 7.1 (d, J=7.9 Hz, 1H), 4.49-4.54 (m, 1H), 4.82 (dd, J=5.2 Hz, 1.2 Hz, 2H), 3.75-3.82 (m, 4H). 2.97 (s, 1H), 2.88 (s, 1H), 2.78 (dd, J=12.1 Hz, 3.1 Hz, 1H), 2.60-2.67 (m, 4H), 2.59 (dd, J=6.0 Hz, 4.3 Hz, 1H); $^{13}$CNMR (75 MHz, CDCl$_3$): δ 180.3, 140.1, 133.1, 128.0, 124.1, 122.7, 122.5, 109.9, 76.1, 77.4, 78.0, 66.6, 62.1, 54.0, 53.4, 42.6; ESIMS: m/z 289 [M+H]+; HRMS: calcd for C$_{16}$H$_{20}$O$_3$N$_2$Na 311.1363, found 311.1366.

Example 33

5-((4-(Pyridin-2-yl)piperazin-1-yl)methyl)-4,5-dihydro-2H-spiro[furan-3,3'-indolin]-2'-one (AB-S)

Yield=78%; viscous liquid; IR (neat): $v_{max}$ 2922, 2856, 1712, 1467, 1220, 1121, 1034, 772 cm$^{-1}$; $^1$H NMR (300 MHz, CDCl$_3$): δ 8.86 (s, 1H), 8.20 (dd, J=8.7 Hz, 1.5 Hz, 2H), 7.28-7.21 (m, 3H), 7.06-6.92 (m, 3H) 4.54 (m, 1H), 4.09 (s, 2H), 3.68-3.42 (m, 5H), 2.98-2.60 (m, 6H), 2.0 (dd, J=9.2 Hz, 3.2 Hz, 1H); $^{13}$CNMR (75 MHz, CDCl$_3$): δ 181.3, 171.4, 159.3, 147.7, 137.4, 134.2, 133.1, 127.9, 122.8, 122.2, 113.2, 109.8, 107.0, 78.0, 76.2, 62.1, 60.3, 54.5, 53.5, 49.9, 43.1; ESIMS: m/z 365 [M+H]+; HRMS: calcd for C$_{21}$H$_{25}$O$_2$N$_4$ 365.1957 found 365.1972.

Example 34

5-((4-(2-Methoxyphenyl)piperazin-1-yl)methyl)-4,5-dihydro-2H-spiro[furan-3,3'-indolin]-2'-one (AB-U)

Yield=78%; solid; 143-145° C.; IR (neat): $v_{max}$ 3246, 2946, 2123, 1714, 1472, 1245, 1025, 765, 682 cm$^{-1}$; $^1$HNMR (300 MHz, CDCl$_3$): δ 8.48 (s, 1H), 7.42-7.26 (m, 5H), 6.98-7.10 (m, 3H), 4.51-4.59 (m, 1H), 4.16 (s, 2H), 3.87 (s, 3H), 3.20-3.10 (m, 4H), 2.90 (dd, J=8.9 Hz, 3.9 Hz, 1H), 2.78-2.84 (m, 4H), 2.68 (dd, J=3.9 Hz, 3.1 Hz, 1H), 2.59 (dd, J=6.0 Hz, 3.1 Hz, 1H), 1.92 (dd, J=3.5 Hz, 3.1 Hz, 1H): $^{13}$C NMR (75 MHz, CDCl$_3$): δ179.1, 152.2, 144.8, 141.3, 142.0, 134.0, 128.3, 129.1, 126.5, 122.9, 122.6, 120.9, 118.1, 10 8.4, 74.1, 77.1, 62.4, 60.35, 55.29, 53.9, 53.6, 50.47, 43.7; ESI-MS: m/z 394 [M+H]+; HRMS calcd for C$_{23}$H$_{28}$O$_3$N$_3$ 394.2127 found 394.2125.

Example 35

5-((4-(4-Methoxyphenyl)piperazin-1-yl)methyl)-4,5-dihydro-2H-spiro[furan-3,3'-indolin]-2'-oneB (AB-T)

Yield=78%; Solid; mp: 146-147° C.; IR (neat): $v_{max}$ 3234, 2925, 2100, 1713, 1470, 1240, 751, 625 cm$^{-1}$; $^1$H NMR (300 MHz, CDCl$_3$): δ 8.46 (s, 1H), 7.34 (d, J=10.2 Hz, 3H), 7.24-7.08 (m, 1H), 6.87-6.93 (m, 6H), 4.51-4.58 (m, J=8.5 Hz, 1H), 4.10 (s, 2H), 3.78 (s, 3H), 3.19 (dd, J=3.9 Hz, 4H), 2.86-2.70 (m, 5H), 1.9 (dd, J=3.5 Hz, 1H); $^{13}$CNMR (300 MHz, CDCl$_3$): δ 192.1, 172.9, 155.9, 145.6, 140.0, 134.5, 128.1, 127.9, 123.9, 123.1, 122.9, 118.2, 114.4, 109.7, 78.1, 77.4, 62.1, 62.0, 55.5, 53.8, 50.4, 43.4, 29.6; ESI-MS: m/z 393[M+H]+; HRMS: calcd for C$_{23}$H$_{28}$O$_3$N$_3$ 394.2105 found 394.2125.

Example 36

5-((4-Benzoylpiperazin-1-yl)methyl)-4,5-dihydro-2H-spiro[furan-3,3'-indolin]-2'-one (AB-Q)

Yield=78%; Thick liquid; IR (neat): $v_{max}$ 3223, 2924, 2855, 1716, 1620, 1282, 1011, 753 cm$^{-1}$; $^1$H NMR (300 MHz, CDCl$_3$): δ 8.61 (s, 1H), 7.41-7.49 (m, 4H), 7.29-7.35 (m, 3H), 7.60-7.51 (m, 2H), 4.51-4.58 (m, 1H), 4.01-4.08 (m, 3H), 3.87-3.93 (m, 2H) 3.77-3.84 (m, 2H), 2.59-2.65 (m, 5H), 2.15 (d, J=5.2 Hz, 1H), 1.90 (dd, J=9.8 Hz, 2.3 Hz, 1H); $^{13}$CNMR (75 MHz, CDCl$_3$): δ 181.0, 173.2, 140.2, 140.0, 135.9, 134.3, 129.6, 128.4, 128.0, 126.9, 123.18, 122.7, 109.8, 78.0, 76.2, 66.7, 62.1, 55.5, 54.4, 53.8, 50.4, 43.1, 29.6; ESI-MS: m/z 392 [M+H]+; HRMS: calcd for C$_{23}$H$_{26}$O$_3$N$_3$ 392.1950 found 392.1968.

Example 37

5-(Thiomorpholinomethyl)-4,5-dihydro-2H-spiro[furan-3,3'-indolin]-2'-one (AB-L)

Yield=78%; Thick liquid; IR (neat): $v_{max}$ 2925, 1720, 1468, 1219, 772, 681 cm$^{-1}$; $^1$HNMR (300 MHz, CDCl$_3$): δ 7.71 (br, s, 1H), 7.54 (dd, J=3.3 Hz, 2.1 Hz, 1H), 7.47-7.22 (m, 2H), 7.05 (d, J=7.6 Hz, 1H), 4.43-4.51 (m, 1H), 4.22 (dd, J=2.7 Hz, 1.2 Hz, 2H), 4.06 (d, J=3.2 Hz, 1.3 Hz, 2H), 2.84-2.89 (m, 4H), 2.71-2.77 (m, 4H), 2.65 (dd, J=4.7 Hz, 3.3 Hz, 1H), 2.55 (dd, J=6.5 Hz, 2.1 Hz, 1H); $^{13}$CNMR (300 MHz, CDCl$_3$): δ 181.2, 140.1, 134.3, 130.9, 128.1, 123.1, 122.8, 109.8, 78.0, 77.3, 62.8, 61.1, 55.4, 43.3, 29.6, 27.7; ESI-MS: m/z 305 [M+H]+; HRMS: calcd for C$_{16}$H$_{20}$O$_2$N$_2$SNa 327.1136 found 327.1136.

Example 38

5-((4-Benzylpiperazin-1-yl)methyl)-4,5-dihydro-2H-spiro[furan-3,3'-indolin]-2'-one (AB-R)

Yield=78%; Solid; mp 141-143° C.; IR (neat): $v_{max}$ 3215, 2926, 2812, 1718, 1684, 1293, 1011, 745 cm$^{-1}$; $^1$HNMR (300 MHz, CDCl$_3$): δ 7.87 (br, s, 1H), 7.24-7.31 (m, 6H), 7.05-6.91 (m, 2H), 4.38-4.42 (m, 1H), 4.21-4.02 (m, 3H), 3.53 (s, 2H), 3.35-3.42 (m, 1H), 2.80-2.39 (m, 6H), 1.82-1.56 (m, 2H), 1.26-1.11 (m, 4H); $^{13}$CNMR (300 MHz, CDCl$_3$): δ 180.4, 139.9, 133.1, 132.3, 132.1, 131.9, 128.4, 128.4, 123.1, 123.0, 122.1, 121.9, 109.9, 109.7, 80.7, 76.1, 69.5, 64.1, 62.5, 60.3, 54.9, 41.2, 38.0; ESIMS: m/z 378 [M+H]+; HRMS: calcd for C$_{23}$H$_{27}$N$_3$O$_2$Na 401.1266 found 401.1236.

Example 39

5-((4-(Bis(4-fluorophenyl))methyl)piperazin-1-yl)methyl)-4,5-dihydro-2H-spiro[furan-3,3'-indolin]-2'-one (AB-V)

Yield=78%; Thick liquid; IR (neat): $v_{max}$ 3220, 2929, 1712, 1504, 1221, 1009, 771 cm$^{-1}$; $^1$H NMR (300 MHz, CDCl$_3$): δ 8.43 (br, s, 1H), 7.40-7.20 (m, 6H), 7.06-6.86 (m, 6H), 4.46-4.53 (m, 1H), 4.23 (s, 1H), 4.04 (s, 2H), 2.80 (dd, J=8.3 Hz, 3.2 Hz, 5H), 2.68-2.39 (m, 6H), 1.91 (dd, J=9.0 Hz, 7.1 Hz, 1H); $^{13}$CNMR (75 MHz, CDCl$_3$): δ 181.3, 162.6, 162.3, 160.7, 140.2, 140.1, 138.1, 138.1, 134.5, 129.2, 129.1, 128.0, 127.9, 124.3, 123.9, 122.1, 115.3, 115.1, 109.7, 77.9, 77.2, 74.3, 62.2, 60.3, 54.5, 53.8, 52.1, 51.4, 43.2; ESI-MS: m/z 490 [M+H]+; HRMS: calcd for $C_{29}H_{29}O_2N_3F_2Na$ 512.2098 found 512.1912.

The present invention provides new class of spirooxindoles which were synthesized from oxindole.

A program was initiated in the laboratory for the design and synthesis of novel spirooxindoles, which can serve as new chemical entities for drug discovery process. In these efforts new spirooxindoles have been synthesized and evaluated for GSK3β activity and the anticancer potential. The synthesis of these compounds has been carried out as described in Scheme 1 using oxindole as the starting substrate.

Biological Activity

In vitro kinase assays screening of the small fragments archived in small molecule compounds library against GSK3β kinase activity has identified three potential fragments with IC50 values below 10 µM. The library of spiroxyindoles prepared based on the identified fragments in the present study was evaluated for their anti-kinase activity of GSK3β. The result indicates that ten compounds have potential to inhibit enzyme activity with $IC_{50}$<5 µM. Though the compounds do not inhibit enzyme activity equivalent to commercially available inhibitors, observed $IC_{50}$ values are better than LiCl standard GSK3β inhibitor. Glycogen Synthase Kinase 3β (GSK3β) is a serine/threonine kinase. It is a multi-functional enzyme, regulating several proteins involved in various signaling pathways including transcription factors, cell cycle/survival regulators and proto-oncogenes. Recent studies suggest that GSK3β may promote tumorigenesis in many cancer types. To confirm specificity of molecules inhibiting intracellular GSK3β, we have determined phosphorylation of glycogen synthase and accumulation of β-catenin. In the HEK293T cells treated with test compounds pGS levels decreased and increased levels of β-catenin confirms its stabilization due to decreased rate of proteasomal degradation. Pancreatic cancer cells have already been reported to express high active pool of GSK3β. Recent studies have revealed that the pancreatic cancer cells are resistant to TRAIL-induced apoptosis. The cytotoxicity results indicate that the compounds significantly increased sensitivity of PANC-1 cells to TRAIL. Further to confirm of cancer cells death by GSK3β inhibitors in combination with TRAIL, we have analyzed cell cycle progression of proliferating PANC-1 cells treated with different concentrations of compounds in the presence or absence of TRAIL. These results are in agreement with the previously reported results that the GSK3β inhibitors sensitize cancer cells to TRAIL induced cell death.

Biological Screening Table

| Identity of the molecule | $IC_{50}$ in µM |
| --- | --- |
| Oxindole | 6.46 ± 0.63 |
| Acetanilide | 6.53 ± 0.52 |
| 2-Pyrrolidine | 8.83 ± 0.49 |
| AB-A | 4.88 ± 1.50 |
| AB-B | 5.31 ± 0.36 |
| AB-C | 3.59 ± 0.98 |
| AB-E | 5.44 ± 1.49 |
| AB-F | 4.68 ± 0.60 |
| AB-K | 4.91 ± 0.56 |
| AB-L | 4.06 ± 1.67 |
| AB-0 | 3.88 ± .01 |
| AB-P | 4.93 ± 0.53 |
| AB-U | 4.92 ± 0.13 |
| Licl | 3.99 ± 0.3 mM |

-continued

| Identity of the molecule | $IC_{50}$ in µM |
| --- | --- |
| SB216763 | 41.82 ± 0.28 nM |
| PIK-75 | 17.6 ± 0.41 nM |

Biological Activity and Screeng

Molecular Modelling:

The docked pose of potent GSK3b with available ligands C, O, and U was predicted by Autodock tools (ADT) and Autodock 4.2. The ligand coordinate file was generated using Chemdraw followed by minimization protocol, performed using steepest descent algorithm. Existing co-crystal structure with defined binding site of GSK3β with PDB ID 4AFJ having 1.98 Å resolution was retrieved from Protein Data Bank (PDB). Crystal structure was used for docking by removing the heteroatoms, hydrogen atoms and kollman charges were added to protein crystal structure using ADT. The pdb files of the ligands and protein structure were converted to pdbqt file using ADT. Docking studies were concentrated on the specific binding site known as ATP binding site. The docking results were further analyzed by using ADT and 3D visualization tool PyMOL.

Activity of recombinant GSK3β is measured using ADP-Glo Kinase assay according to supplier's standard protocol with minor modifications in 384 well format. Briefly, kinase reaction mixture was prepared by adding 5 mg of recombinant enzyme, 2 µM ATP, 1 µg of enzyme substrate along with test compound or DMSO to a final volume of 5 µl. The kinase reaction was performed by incubating the mixture at room temperature for 17 mins. To correct reaction back ground a substrate blank reaction was also performed. ADP glow reagent (equal volume to reaction mixture) was added to the reaction mixture to deplete any unused ATP added to the kinase reaction and incubated at further 40 min at 27° C. Then 10 µl of kinase detection reagent was added followed by incubation for 30 min at 27° C. to convert ADP to ATP and introduce luciferase to measure kinase activity. The luminescence was measured using luminometer (Perkin Elmer) which is directly proportional to ADP generated in kinase reaction. To determine the amount of ADP produced in kinase reaction and calculate specific activity of the enzyme, a conversion curve is prepared by serial dilution of ADP and ATP mixture. Specific activity of the GSK3β was calculated using the following equation.

(ADP(kinase reaction)−ADP(substrate blank)) in mmol)/(Reaction time in min)×(GSK3β in mg).

Cell Culture:

The cell pLen,(JZ)-Top.Luc, pLen-TopFlash.dGFP 293T stable cells were generated in myoclinic USA, panc-1 used in the current study were obtained from ATCC (Manassas, USA) and cultivated in DMEM (Sigma) supplemented with 10% fetal bovine serum, 100 units/mL penicillin and streptomycin. To avoid for mycoplasma contamination in cell cultures, cells were regularly tested using the MycoAlert Kit (Cambrex Bio Science Rockland, Inc., Rockland, Me., USA).

Luciferase Assay:

To determine inhibitory potential of hit molecules from primary screening against intracellular GSK3β, a reporter assay system has been established using pLenti(JZ)-Top.luc vector and HEK293T cells. The stable cell lines having integrated TCF/LEF luciferase reporter gene were selected in the presence of suitable antibiotics in the culture medium. To test activity of hits against GSK3β, stable cells were treated with different concentrations (0-100 μM) of either compounds or standard positive controls. Cells were allowed to grow for further 24 hrs under standard culture conditions. Upon termination, cells were harvested directly in 1×CCl buffer. To determine luciferase activity, 5 μl of cell lysate was mixed with 20 μL of assay reagent (company name) containing luciferase substrate in a MTP well pate (384 well format) and incubated for 5 mins in dark. The luciferase activity was determined by measuring luminescence at wavelengths in multimode reader. The protein concentration of the lysates was estimated by Bradford assay to normalize luciferase activity with protein present in the lysates. Then the relative luciferase activity was calculated according to control cells treated with DMSO set to 1. All experiments were performed in triplicates and the mean values with ±SD are presented here.

Cell Viability:

Cell viability was measured using Sulforhodamine B assay. The cytotoxic effect of the compounds with GSK3β inhibitory potential was tested against PANC-1 cells. Initially, the PANC-1 cells were seeded in flat bottom 96-well plate (5000 cells/100 μL) in complete medium and cultured for 18 hrs under standard conditions. After 18 h the cells were treated with either the different concentration of compounds, standard drugs or DMSO as solvent control. The final DMSO concentration to cells was maintained <2% in all cytotoxic assays. Each compound was tested in triplicate and the cytotoxicity was determined as the average of that triplicate. Further, the plates were incubated for another 48 h in an incubator maintained at 37° C. with a constant supply of 5% $CO_2$. The cells were fixed using 10% TCA and incubated for 1 h at 4° C. Then the plates were rinsed carefully with MQ water and air dried at room temperature. To all the wells of MTP plate 0.057% SRB solution was added and kept for approximately 30 min before it was rinsed off using 1% acetic acid. The plates were then air dried and 100 μL of 10 mM tris base was added to each well to solubilize the SRB before absorbance was measured at 510 nm. The measure of absorbance is directly proportional to cell growth and is thus used to calculate % reduction in the rate of cell proliferation according to control DMSO treated cells. All experiments were performed in triplicates; mean % age proliferation values with ±SD were plotted here.

Treatment of PANC-1 Cells with GSK3β Inhibitors

The compounds inhibiting GSK3β activity in-vitro added to PANC-1 cells to determine their potential against intracellular GSK3β signalling pathways in cancer cells. Briefly, PANC-1 cells were plated in 60 mm plates (100,000 cells/4 mL) and cultured in the standard DMEM medium containing 10% serum. After culturing for 18 hrs, different concentrations of test compounds or standard controls prepared in DMSO were added to culture media to achieve final concentration 0 to 100 μM of compound to cells. Cells were further continued to grow for 48 h with constant supply of 5% $CO_2$ in humid incubator. The time course (0 to 48 h) experiment was carried out simultaneously with fixed concentration of compound showing 50% growth inhibition. At the end of the experiments, all cells were scraped directly in cold PBS and washed for 3 times before lysis directly in 2D lysis buffer (8M urea, 2M thiourea, 4% CHAPS, 4 mM tris base and 65 mM DTT) for isolation of proteins to perform western blots. The protein concentration was determined by modified Bradford assay.

Western Blotting:

To perform western blot, protein extracts were separated on 12% SDS-PAGE and electrophoretically (1 $mA/cm^2$ membrane for 1 hr) transferred onto the nitrocellulose membrane by semi-dry method. After protein transfer, membrane was stained with Ponceau S solution (0.2% Ponceau S in 3% Trichloroacetic acid) for 2 min to see efficiency of electrophoretic transfer. The membrane was destained in $ddH_2O$ to visualize the protein bands and further destained with TBST (20 mM Tris, 138 mM NaCl, pH 7.6 and 0.1% Tween 20) for blotting. To avoid non-specific detection of target proteins, blotted membranes were blocked with BSA (3% BSA in TBST solution). All antibodies against specific protein targets of interest were purchased from Cell Signaling Technology, USA if not mentioned specifically. Then the blots were incubated with antibodies prepared in blocking buffer (1:1000 Antibody to blocking buffer dilution) for 18 h with constant shaking at 4° C. Three washing steps in PBS each for 5 mins removed the excess and non-specific antibodies. For visualization, blots were incubated with secondary antibody conjugated to either horseradish peroxidase or alkaline phosphatase [anti-(mouse IgG) or anti-(rabbit IgG), diluted 1:5000 in TBST] for 1 h at room temperature. After three washes in PBS, the reaction was developed either by addition of LumiGLO substrate (Cell Signaling Technology) followed by capturing on X-ray film or addition of chromogenic NBT (nitro-blue tetrazolium chloride) and BCIP (5-bromo-4-chloro-3'-indolylphosphate p-toluidine salt) substrate for alkaline phosphatase developing purple colored bands. The blots were scanned for densitometry performed using Image-J program.

NFkB Luciferase Assay:

In order to evaluate the effect of GSK3β inhibition on NF-kB activity, a reporter assay has been performed in the presence of identified inhibitors. To perform reporter assays, PANC-1 cells were cultured in a 48 well plate (16000 cells/well) overnight. Following day, cells were transfected with appropriate amount NF-kB reporter construct using lipofectamine 2000 as per manufacturer's protocol. After 16 hrs of post transfection cells were treated with identified GSK3β inhibitors and positive controls. After 48 h of treatment, cells were harvested in directly 1×ccl buffer. For measuring luciferase activity, 5 μl of cell lysate was mixed with 20 μl of assay reagent containing substrate for luciferase in MTP well plate as per manufacturer's protocol. The luciferase activity was determined by measuring luminescence at wavelengths in multimode reader. The protein concentration of the lysates was estimated by Bradford assay to normalize luciferase activity with protein present in the lysates. Then the relative luciferase activity was calculated according to control cells treated with DMSO set to 1. All experiments were performed in triplicates and the mean values with ±SD are presented here.

Cell Cycle Analysis of PANC-1 Cells Treated with GSK3β Inhibitors:

To determine effect of GSK3β inhibitors on cell death and/or cell cycle progression, PANC-1 cells were treated with identified molecules with or without TRAIL. Upon treatment with compounds in combination with TRAIL, PANC-1 cell death was determined with propidium iodide (PI) uptake measured by Flow cytometry. Treated cells were harvested in cold PBS and fixed in 70% ethanol at −20° C. for overnight. The fixed cells were by centrifugation and re-suspended in PI (50 mg/mL) solution containing RNase (0.1 mg/mL) and Triton X-100 (0.05%). The cells were incubated in dark for 1 h at room temperature. The excess PI was washed out using PBS, the resultant PI uptake was analyzed by FACS Caliber System (BD Bio-science, Erembodegem, Belgium) in an FL-2 fluorescence detector (10000 events were recorded for each condition). Flow cytometry data was analyzed using FCS express 4 software (De Novo Software, Los Angeles, Calif., USA).

Determination of caspase-3 and -9 activities in PANC-1 cells treated with GSK3β inhibitors: Both Caspase-3 and -9 activities were measured 48 h after treating the PANC-1 cells with either GSK3β inhibitors alone or in combination with TRAIL. Specific fluorogenic substrates Ac-DEVD-AMC and Ac-LEHD-AFC, were used specific to Caspase-3 and -9 respectively. The harvested cells were directly lysed in caspase lysis buffer (50 mM HEPES, 5 mM CHAPS, 5 mM DTT, pH 7.5). The lysates were mixed with respective substrates prepared standard buffer (20 mM HEPES (pH 7.5), 0.1% CHAPS, 2 mM EDTA and 5 mM DTT) and incubated for 2 hrs at 37° C. in dark. The cleavage of substrates releasing AMC and AFC was detected by multi-mode reader (Perkin Elmer) using an excitation/emission wavelengths 380/460 nm for AMC and, 400/505 nm for AFC. The fluorescence readings were normalized to total protein concentration. The observed fluorescence is directly proportional to activity of caspase-3 and -9. The relative caspase activities were calculated as the ratio of values between DMSO treated and compound or standard drug treated cells.

Colony Formation Assay:

To determine the efficiency of GSK3β inhibitors in combination with the TRIAL on anchorage independent growth of PANC-1 cells soft agar assay were performed [3]. The base agar (0.5%) was prepared by mixing equal amounts of 1% agar with 2× media (20% FBS and 2× antibiotics) filled in 6-well plate. Simultaneously, PANC-1 cells (14000/well) mixed with 2× media containing different concentrations of identified compounds alone or in combination with TRAIL mixed with 0.7% of sterile agar to achieve final concentration of 50.35% top agar. The cell suspension was spread on solidified base agar. Then the plates were incubated in $CO_2$ incubator for 14 days and the cells were fed with fresh media containing respective concentration and combination of TRIAL every 3 days. Upon termination (after 14 days of incubation) plates were stained with 0.005% of crystal violet for 1 h and excess stain was removed by washing with MQ. The number of blue colonies were counted using olympus Xi71 microscope.

Results and Discussion:

Validation of Docking Pose:

The docking studies were concentrated in the specific ATP binding site, which is located between the N-terminal β-barrel domain and the C-terminal helical domain. The results suggest that three compounds are binding in the ATP binding site of GSK3β (Fig A) which showed interaction with the key residue VAL135. The compound C was interacting with ATP binding site of GSK3β beta pleated sheets. From the results it was observed that the presence of intermolecular H-bonding network between the CO and NH of the indole ring to the backbone NH of V135 and CO of D133 respectively. The binding energy is significantly low with score −9.2 Kcal/mol. Further the docking results from the compound C displayed similar binding mode with the presence of H-bonding network between CO of indole to NH of V135 and NH of Indole to CO of D133 with favourable docking score −7.5 Kcal/mol. For the compound U the H bond interaction was observed between the CO and NH of the indole ring to the backbone NH of V135 and NH of N65 with a favourable docking score −7.07 Kcal/mol. From the results, it is inferred that three compounds were interacting with specific ATP binding region and hinge residue V135 of GSK3β with favourable docking score and showed the better activity of the compounds. The docking poses were generated through PyMOL and the complex of three compounds interacting with binding site was pictorially represented in Figure A.

Spirooxindoles Inhibits GSK3β Kinase Activity:

In invitro kinase assays screening of the small molecules archived in a compound library against GSK3β kinase activity has identified three potential fragments with $IC_{50}$ values below 10 μM (Table 01). The library of spirooxindoles prepared in the present study was evaluated for their anti-kinase activity of GSK3β. The result indicates that ten compounds have potential to inhibit enzyme activity with $IC_{50}$<10 μM (Table 01). Though the compounds do not inhibit enzyme activity equivalent to commercially available inhibitors, observed $IC_{50}$ values are better than LiCl standard GSK3β inhibitor.

Figure 2:
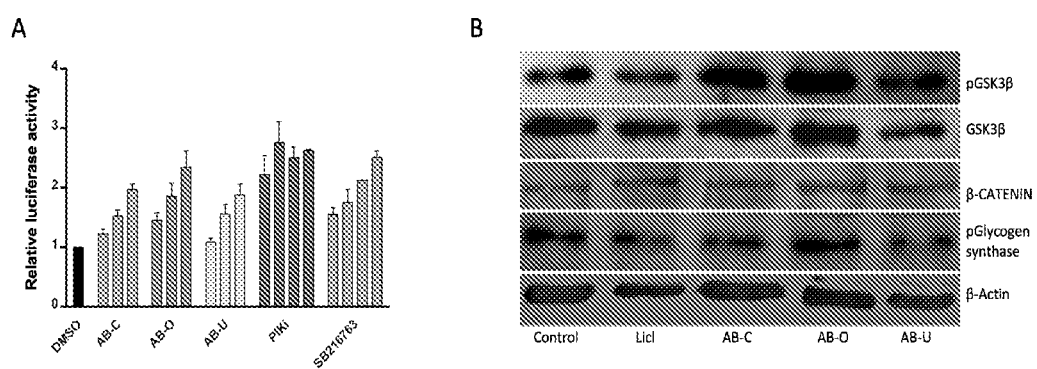
FIG. 2: GSK3β inhibition sensitizes pancreatic cancer cells (PANC-1) to TRAIL.

Activity Against Intracellular GSK3β:

GSK3β is a part of the canonical β-catenin/Wnt pathway involved in promoting cell proliferation. GSK3β phosphorylates β-catenin targeting it for proteasomal degradation. Upon GSK3β inhibition, unphosphorylated β-catenin (active form) is translocated into nucleus, which then binds to tcf and lef family transcription factors and initiates transcription of target genes. Based on this principle we have established stable reporter cell line to monitor activation of wnt pathway. To determine intracellular efficiency of GSK3β inhibition, HEK293T cells (stably expressing tandem repeats of the TCF/LEF transcriptional response element followed by the firefly luciferase) treated with selected compounds. The increased luciferase activity is a measure of activation of Wnt pathway (downstream of GSK3β) confirmed that the three compounds potentially inhibiting GSKβ in a dose dependent manner (FIG. 2A). GSKβ usually inhibits the activity of its downstream target by protein phosphorylation of a protein onto threonine and serine amino acids residues. The immediate target of GSK3β is glycogen synthase (GS) which is involved in glycogen synthesis there by regulating energy metabolosm [4] (Frame and Cohen, 2001). To confirm specificity of molecules inhibiting GSK3β, we have determined phosphorylation of glycogen synthase and accumulation of β-catenin. In the HEK293T cells treated with test compounds pGS levels are decreased and also increased levels of β-catenin confirms its stabilization due to decreased rate of Proteasomal degradation (FIG. 2B). In the drug discovery pipeline, many of the newer molecules identified in target based approach often fail while hit to lead progression due to cell permeability. Therefore it is important to select molecules which can easily permeable through cell wall. The results obtained here confirmed that the selected compounds already fulfilled some important criteria such as, cell permeability and good inhibitory potential against endogenous GSKβ.

Figure 3:
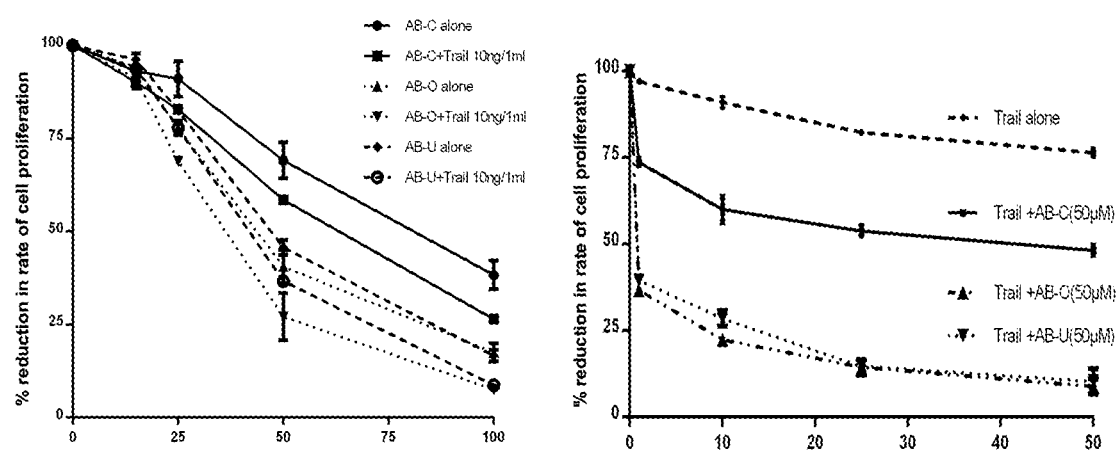
FIG. 3: (A) The cytotoxicity results indicate that the compounds significantly increased sensitivity of PANC-1 cells to TRAIL; (B) The compound AB-C is not effective compared to remaining compounds

Pancreatic cancer cells have already been reported to express high active pool of GSK3β [5]. Recent studies have revealed that the pancreatic cancer cells are resistant to TRAIL-induced apoptosis [6]. GSK3β inhibition sensitizes pancreatic and prostate cancer cells to TRAIL mediated apoptosis [7,8]. To determine efficiency of the identified molecules against proliferation of cancer cells, PANC-1 cells were treated with different concentrations of the identified compounds alone or in combination with TRAIL (10 ηg/mL). The cytotoxicity results indicate that the compounds significantly increased sensitivity of PANC-1 cells to TRAIL (FIG. 3A). Among the three potential compounds tested AB-O and AB-U inhibited the cell growth by 50% at 30 μM in combination with TRAIL (10 ηg/mL) where as AB-C is less effective compared to other molecules. Higher concentration of test compounds AB-O and AB-U showed more than 50% growth inhibition even at low concentration of TRAIL (1 ηg/mL). The compound AB-C is not effective compared to remaining compounds (FIG. 3B). TRAIL alone (10 ηg/ml) did not cause any significant cell death in PANC-1 cells but TRAIL combination with GSK3β inhibitors in increasing concentrations cause significant decrease in cell viability.

Figure 4:
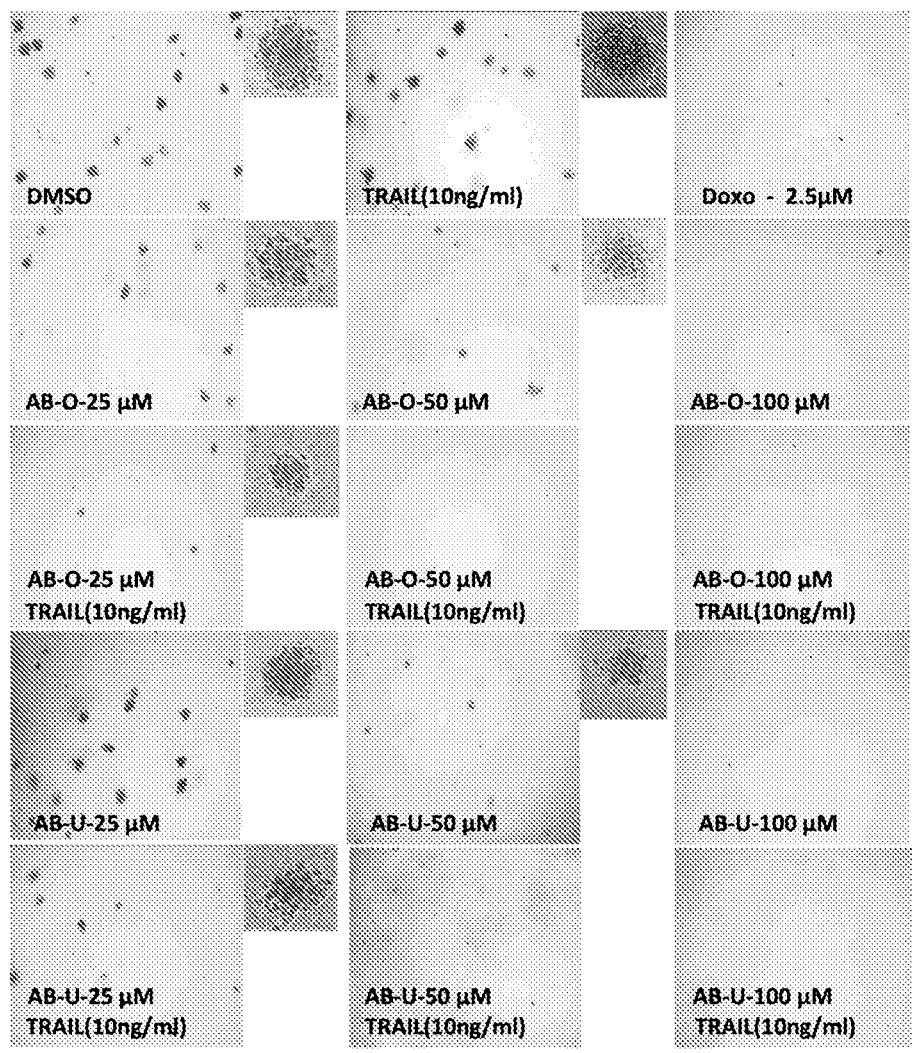
FIG. 4: The TRAIL alone did not show effective inhibition on colony formation at the concentration 10 ηg/mL used

To determine the long-term effects of the identified compounds against GSK3β on proliferation and anchorage independent growth of the PANC-1 cells soft agar assay (clonogenic assay) was performed. The cells were treated and fed continuously with compounds alone or along 10 ηg/mL of TRAIL. Results clearly showed effect of AB-O and AB-U on formation of colonies by PANC-1 cells. From the clonogenic assays, a dose-dependent inhibition was observed on treatment of cells with AB-O and AB-U. Interestingly, both the compounds showed more effective inhibition of colony formation in the presence of TRAIL confirmed by size and morphology of the clones observed. The TRAIL alone did not show effective inhibition on colony formation at the concentration 10 ηg/mL used (FIG. 4). It has been reported that the clonogenic assay correlates well with in vivo assays of tumorigenicity in nude mice [9] indicating the high efficacy of AB-O and AB-U towards inhibition of PANC-1 cells growth.

Figure 5:
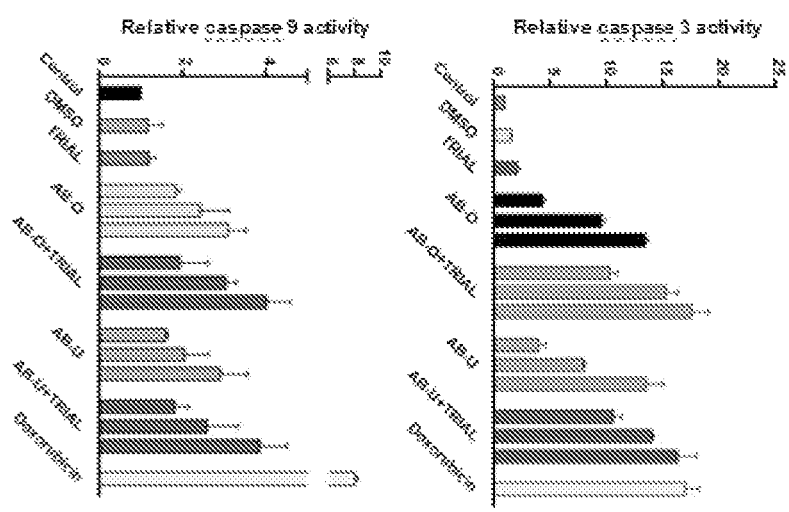
FIG. 5: Activity AB-O and AB-U on cellular GSK3β signalling.

Further to confirm of cancer cells death by GSK3β inhibitors in combination with TRAIL, we have analyzed cell cycle progression of proliferating PANC-1 cells treated with different concentrations of compounds in the presence or absence of TRAIL. The histograms of cell cycle progression presented in the supplementary FIGS. 01 and 02 suggest that both the compounds AB-O and AB-U induces more cell death in combination with TRAIL than compounds alone or TRIAL alone. The increase in the % of cells in subG1 indicates PANC-1 cells death. These results are in agreement with the previously reported results that the GSK3β inhibitors sensitize cancer cells to TRAIL induced cell death. TRAIL induced apoptosis of cancer cell is mediated by the activation of procaspases to active caspases by proteolysis. To glean more information weather the compounds show synergistic effect on activation of caspase cascade to induce apoptosis, we have measured caspase-3 and -9 activities in PANC-1 cells treated with compounds along with TRAIL. The obtained result suggests that the combinatorial treatment of PANC-1 cells is more effective even at lower concentration of the compounds than individually in activation of both the caspases (FIG. 5). Taken together it is also clear that the apoptosis of PANC-1 cells treated with GSK3β inhibitors is through mitochondiral dependent pathway.

Figure 6:
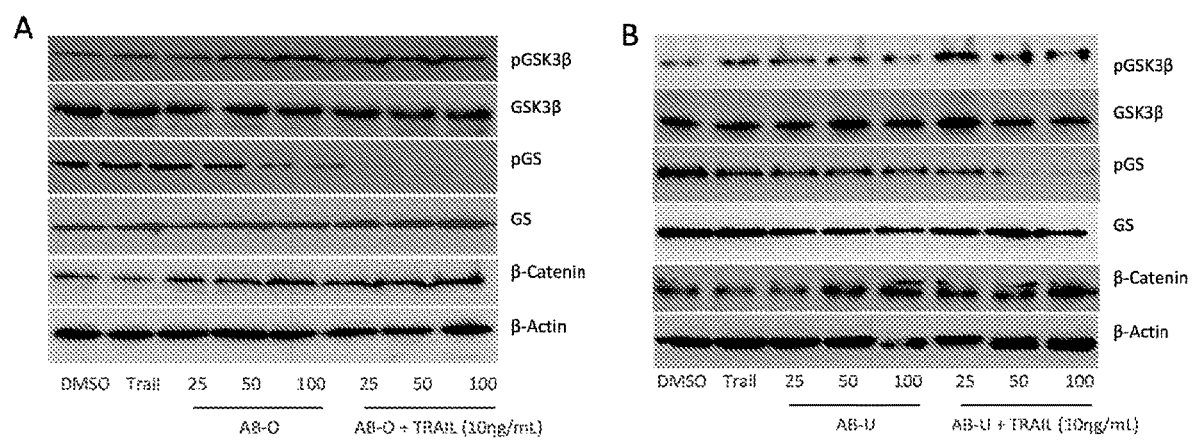
FIG. 6: Shows the Effect of AB-O and AB-U in combination with TRAIL on cellular GSK3β signalling.

GSK3β is a Multifunctional enzyme which phosphorylates several of its downstream substrates. GSK3β is actively involved in multiple signaling pathways thereby regulation of cell survival, proliferation, migration, inflammation, immune responses glucose regulation and insulin signaling, neuronal function and oncogenesis to embryonic development. Of the several substrates, some of the key targets are glycogen synthase, beta catenin and tau proteins [10,11]. To confirm potential of AB-O and AB-U in combination with TRAIL on cellular GSK3β signalling, first we have measured phosphorylation of GSK3β. Increased phosphorylation of GSK3β on $9^{th}$ serine residue silences its kinase activity (FIGS. 6A&B). In our results we observe the synergistic effect of both AB-O and AB-U in combination with TRAIL in GSK3β inhibition by phosphorylation. Phosphorylation of GSK3β at serine residue will create a pseudo substrate conformation which folds and bound to the catalytic site of the enzyme and prevents binding of substrates to active site, there silences the GSK3β activity. Further, we measured phosphorylation of GS a primary substrate of GSK3β which is involved in glycogen metabolism. Here, p-GS was significantly decreased with increasing concentrations of AB-O and AB-U, where total GS remains unaffected. The compounds are more effective when the PANC-1 cells are treated in combination with TRAIL (FIGS. 6A&B).

GSKβ participates in regulation of wnt pathway via phosphorylation of β-catenin. Active GSK3β phosphorylates β-catenin targeting it for ubiquitin mediated proteolysis. Inhibition of GSK3β causes the stabilization and accumulation of β-catenin in cytoplasm and further translocates into the nucleus. Nuclear β catenin along with TCF/LEF elements continuously drive transcription of its target genes. Nuclear β-catenin is implicated in progression of several types of cancers such as prostate cancer, basal cell carcinoma, head and neck cancers and medulloblastoma. As anticipated, β-catenin levels are elevated in PANC-1 cells exposed to GSK3β inhibitors compared to the control (DMSO) treated cells (FIGS. 6A&B). Interestingly, the synergistic effect of GSK3β inhibitors along with TRAIL on β-catenin levels is very significant compared to molecules or TRAIL alone.

Figure 7:
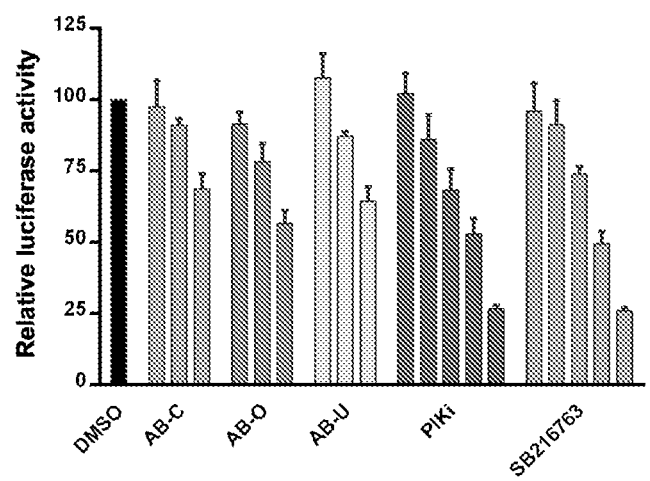
FIG. 7: Effect of AB-O and AB-U on expression of NFkB target genes involved in cell survival.

Effect of GSK3β Inhibition on NFkB Transcriptional Activity:

Daniel D. Billadeau et al reported that active GSK3β arbitrate cell proliferation and viability of the pancreatic cancer cells through NFkB pathway. NFkB is constitutively activated in most of the cancers including pancreatic cancer enhancing transcription of several genes responsible for cell survival [5]. To determine whether the compounds AB-O and AB-U are NFkB dependent or independent in controlling growth of PANC-1 cells we have performed NFkB specific reporter assays. As showed in FIG. 05, luciferase activity that is a measure of NFkB activity is significantly decreased with dose dependent inhibition of GSK3β using AB-O and AB-U (FIG. 7). Both the standard controls used also showed same effect in the PANC-1 cells.

Effect of AB-O and AB-U on expression of NFkB target genes involved in cell survival:

In cell viability assay we have observed significant reduction in cell viability upon the GSK3β inhibition by AB-O and AB-U in combination with TRAIL. In NFkB reporter assays we have observed that the inhibition of GSK3β reduces NFkB activity. Altered transcriptional activity of NFkB may result in differential expression of its targeted genes such as anti-apoptotic proteins BCL2 and XIAP. Based on this result, we have measured the expression antiapoptotic proteins BCL2 and XIAP upon the inhibition of GSK3β. As showed in FIGS. 8 A&B, we can clearly observe a significant decrease in the BCL2 and XIAP levels of PANC-1 cell treated with inhibitors. The compounds AB-O and AB-U clearly showed synergistic effect on the BCL2 and XIAP levels. In presence of TRAIL both the compounds lowered expression of BCL2 and XIAP more effectively than TRAIL alone or compound alone. Shadi Mamaghani et al reported that cells over expressing the BCL2 an antiapoptotic protein are resistant to TRAIL induced apoptosis. Down regulation of BCL2 upon the GSK3β inhibition may sensitize the cells to TRAIL.

Figure 8:
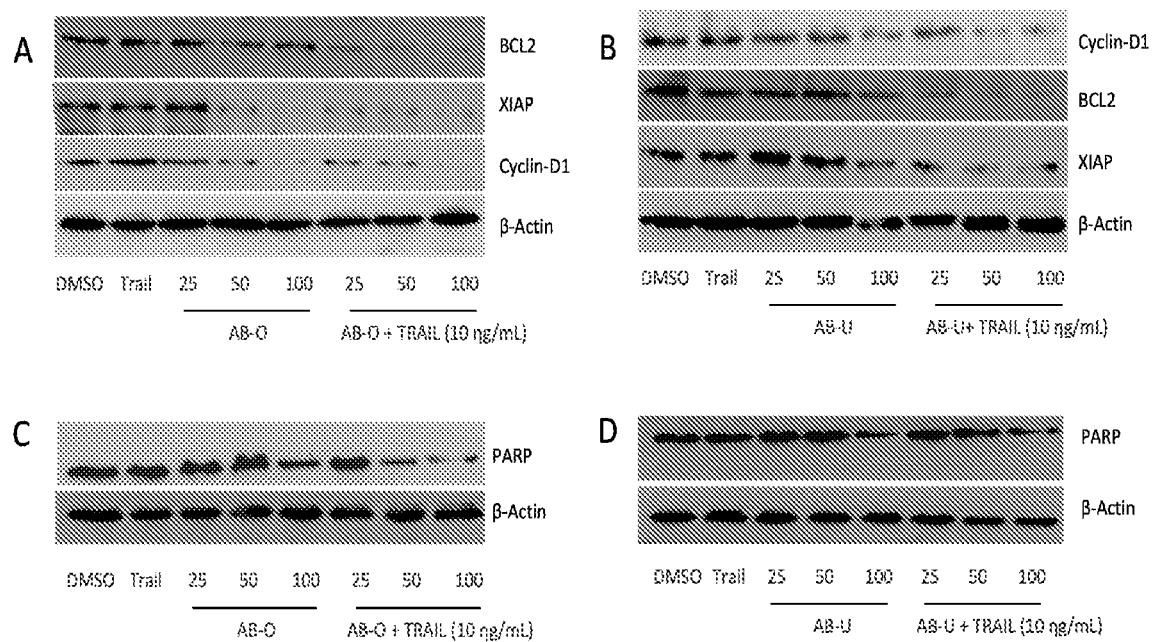
FIG. 8: molecules AB-O and AB-U inhibiting cellular GSK3β sensitizing the PANC-1 to TRAIL inducing apoptosis.

Further, we have measured expression of the Cyclin D1 in PANC-1 cells upon GSK3β inhibition. Both the compounds AB-O and AB-U significantly reduced Cyclin D1 levels in combination with TRAIL (FIGS. 8 A&B). Cyclin D1 is a cell cycle regulating protein involved in control of cancer cell proliferation. Taken together, the results obtained indicate that the molecules AB-O and AB-U inhibiting cellular GSK3β sensitizing the PANC-1 to TRAIL inducing apoptosis.

Discussion:

Glycogen Synthase Kinase 3β (GSK3β) is a serine/threonine kinase. It is a multi-functional enzyme, regulating several proteins involved in various signalling pathways including transcription factors, cell cycle/survival regulators and proto-oncogenes. Recent studies suggest that GSK3β may promote tumorigenesis in many cancer types. Its abberent over expression was found in human pancreatic (H), colon (I), prostate (J), leukaemia (K), thyroid (l), brain (M) and ovarian (N) cancer cells. Billadeau et. al. reported for elevated levels of GSK3β in many pancreatic cancer cell lines including PANC-1. In ovarian cancer patients GSK3β is significantly over expressed and active GSK3β promotes proliferation of ovarian cancer cells (N). This led to the current study design aiming to identify new GSK3 β selective inhibitors and its inhibition is an attractive approach for effective treatment of pancreatic cancer.

From the series of synthesized compounds, AB-O, AB-C and AB-U showed potent inhibition of GSK3β in in-vitro kinase assays. To determine their efficiency against intracellular GSK3β; we observed that the treatment of PANC-1 cells with AB-O, AB-C and AB-U significantly decreased phosphorylation of GSK3β. Further, accumulation of β-catenin in these cells confirmed that these three molecules were effective against GSK3β in PANC-1 cells. Cell viability assays have confirmed that AB-O and AB-U are more effective in inhibiting cell proliferation. These results are in line with the previous studies that the inhibition of GSK3β decreases rate of cell proliferation and survival in many cancers such as CLL (k), pancreatic (h), colon (i), ovarian (n), thyroid (l) and brain (m).

Chemotherapeutic drugs are also known to be toxic to normal healthy cells. which is why it has become prerequisite in present time to develop effective strategies that increase the target based therapeutic potential of anticancer drugs with decreased toxicity to normal healthy cells, more efforts are being directed towards combination chemotherapy. Tumor necrosis factor-related apoptosis-inducing ligand (TRAIL) is known to induce apoptosis in various human cancer cell lines but not in normal healthy cells. Prostate and pancreatic cancer cell were resistant to TRIAL. David J. McConkey et al were measured the TRIAL dependent apoptosis in panel of 9 pancreatic cancer cells among them PANC-1 was shown to be less sensitivity to trail mediated apoptosis. in our study we measured growth inhibitory effects of new GSK3 inhibitors in combination with trail (10 ng/mL), based on our data there was significant decrease in cell viability was observed in combination with TRAIL.

GSK3 also plays a role in cell proliferation and apoptosis through several pathways. GSK regulates the various transcription factors which initiate the transcription of several proto oncogens. Present reports revealing that GSK3 positively regulates NFkB-dependent genes responsible for proliferation and anti-apoptotic signals in many cancers like pancreatic (d), and leukemia (K). In order to conform the above findings we measured the NFKB activity upon GSK3 inhibition, as we presented in FIG. 8 NFKB activity was increased. Further we have measured the expression of NFKB target genes whose were involved in apoptosis and cell proliferation. Both genes bcl2 and xiap were decreased in a dose dependent manner of AB-O and AB-U. Cyclin-dl, cell cycle regulator which promotes cell proliferation was also reduced.

Recent studies showing pancreatic cancer cells were resistance to TRAIL, because of the increased expression of an anti-apoptotic protein XIAP. Inhibition of XIAP, sensitizes the pancreatic cancer cells to TRIAL mediated apoptosis in invitro and in vivo. There were many studies supporting the role of NFKB in trail resistance. It was explained by nfkb positively regulates the transcription of anti-apoptotic proteins such as XIAP, BCL-2, BCL-XL, and MCL-1 in cancer cells GSK mediates binding NFKB P65 subunit to the promoters of an anti-apoptotic genes BCL2 and XIAP, so inhibition of GSK reduces the expression these anti-apoptotic genes, there by inhibition of GSK sensitize the pancreatic cancer cells to trail mediated apoptosis.

To conform whether AB-O and AB-U cause cell death in pancreatic cancer cells, we measured the cell death using FACS. The results indicate, panc-1 cells were showing cell death even at 25 uM concentration of AB-O, AB-U and death was increased with increasing doses of GSK inhibitors and in combination with the trail. Further to investigate, whether the cell death is because of apoptosis, we have measured the activity of caspases post exposure GSK inhibitors, both caspase3 and 9 were activated. Next we measured long term effects of GSK inhibitors in combination with the trail on panc-1 pancreatic cancer cells. The results showed that GSK inhibition reduces the anchorage of independent growth cancer cells this as an important future of cancer cells. Finally our data supports the anti-apoptotic role of GSK in pancreatic cancer, combination of GSK inhibition in combination with TRAIL or other drugs like gemcitabine may serve as chemotherapeutic agents to treat pancreatic cancer.

Advantages of the Invention

The advantages of the method are given below.

The main advantage of the present invention is that it provides spirooxindole derivatives.

The advantage of the present invention is that it provides an efficient process for the preparation of diversely substituted novel spirooxindole derivatives.

Another advantage of the present invention is the use of these spirooxindole compounds as GSK3β inhibitors.

The spirooxindole compounds prepared are novel synthetic derivatives, which are useful as GSK3β inhibitors for their anticancer potential.

We claim:
1. A Spirooxindole compound of formula I

Formula I

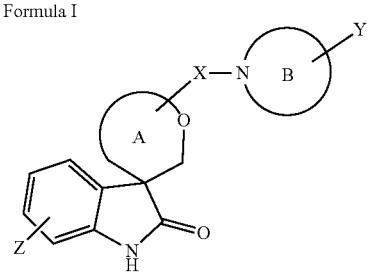

wherein
Z is hydrogen, halogen, hydroxy, alkoxy, cyano, or nitro;
Ring A is a five, six or seven membered ring optionally containing an additional hetero atom;
X is either absent or $CH_2$;

Ring B is a triazole or a cyclic amine optionally internally substituted with one or more hetero atoms and optionally substituted with a single substituent Y;

Y is hydrogen, halogen, azide, hydroxymethyl, aryloxy, hydroxy, alkoxycarbonyl, amide, amino, alkyl, phenyl, pyridinyl, benzyl, or benzoyl, aminoalkyl, Y is optionally substituted with one or more of substituents $Y^a$, wherein $Y^a$ is halogen, hydroxy, alkoxy, alkyl, phenyl, pyridinyl, benzyl, benzoyl, aryloxy, nitro, cyano, alkoxycarbonyl or aldehyde;

each $Y^a$ is optionally substituted with one or more substituents $Y^b$, wherein $Y^b$ is halogen, hydroxy, alkoxy, alkyl, phenyl, pyridinyl, benzyl, benzoyl, aryloxy, nitro, cyano, alkoxycarbonyl, or aldehyde; and each $Y^b$ is optionally substituted with one or more substituents $Y^c$, wherein $Y^c$ is of alkoxycarbonyl, halogen or alkyl.

2. The compound as claimed in claim 1, represented by the compound of formula II Formula II

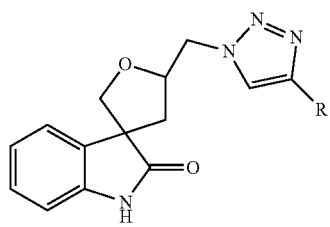

wherein

R is hydrogen, hydroxymethyl, aryloxy, hydroxy, alkoxycarbonyl, amide, amino, alkyl, phenyl, pyridinyl, benzyl, or benzoyl;

R is optionally substituted with one or more substituents $R^a$, wherein $R^a$ is halogen, hydroxy, alkoxy, alkyl, phenyl, pyridinyl, benzyl, benzoyl, aryloxy, nitro, cyano, alkoxycarbonyl, or an aldehyde;

each $R^a$ is optionally substituted with one or more substituents $R^b$, wherein $R^b$ is halogen, hydroxy, alkoxy, alkyl, phenyl, pyridinyl, benzyl, benzoyl, aryloxy, nitro, cyano, alkoxycarbonyl, or aldehyde; and each $R^b$ is optionally substituted with one or more substituents $R^c$, wherein $R^c$ is alkoxycarbonyl, halogen or an alkyl.

3. The compound as claimed in claim 1, selected from the group consisting of:

(AB-O) Ethyl 2-methyl-6-(2((1-(2'-oxo-4,5-dihydro-2H-spiro[furan-3,3'-indoline]-5-yl)methyl)-1H-1,2,3-triazol-4-yl)methoxy)phenyl)nicotinate

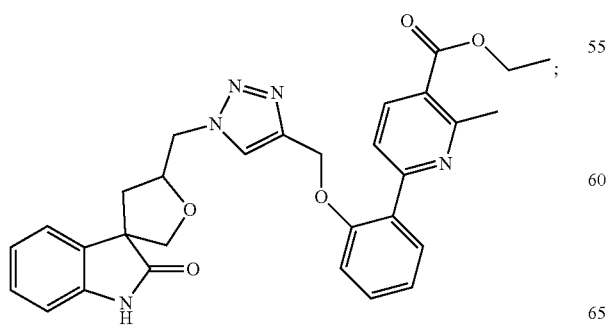

(AB-M) Ethyl 6-(5-fluoro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate

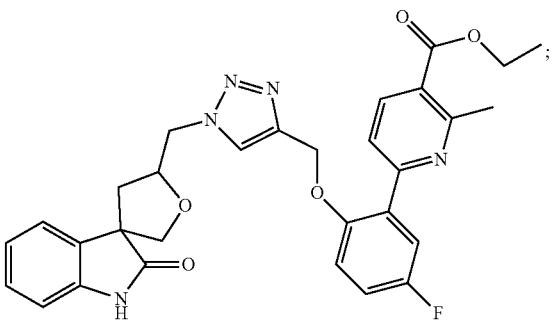 [SMILES: CCOC(=O)c1ccc(-c2cc(F)ccc2OCc2cn(CC3CC4(CO3)C(=O)Nc3ccccc34)nn2)nc1C]

(AB-N) Methyl-6-(5-chloro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate

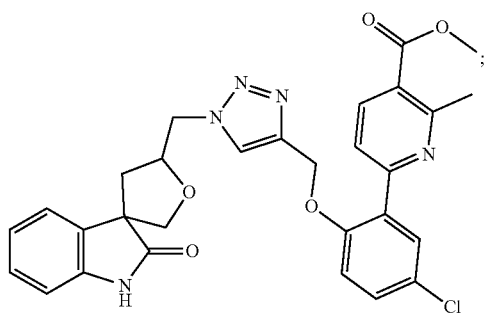 [SMILES: COC(=O)c1ccc(-c2cc(Cl)ccc2OCc2cn(CC3CC4(CO3)C(=O)Nc3ccccc34)nn2)nc1C]

(AB-P) 2-((1-((2'-Oxo-4,5-dihydro-2H-spiro[furan-3,3'-indoline]-5-yl)methyl)-1H-1,2,3-triazol-4-yl)methoxy)benzaldehyde

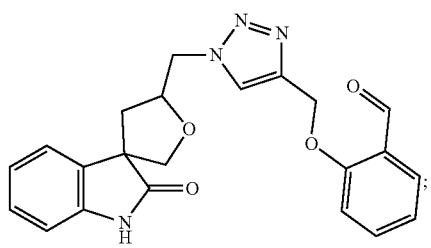 [SMILES: O=Cc1ccccc1OCc1cn(CC2CC3(CO2)C(=O)Nc2ccccc23)nn1]

(AB-W) Ethyl-6-(3,5-dichloro-2-((1-((2'-oxo-4,5-dihydro-2H-spiro[furan-3,3'-indoline]-5-yl)methyl)-1H-1,2,3-triazol-4-yl)methoxy)phenyl)-2-methylnicotinate

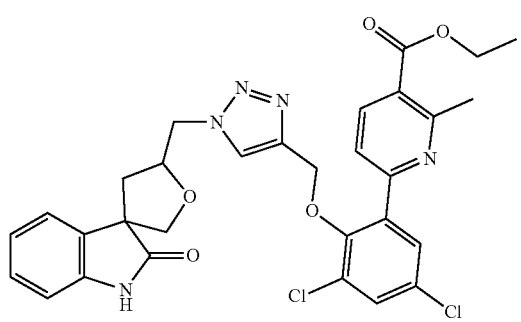 [SMILES: CCOC(=O)c1ccc(-c2cc(Cl)cc(Cl)c2OCc2cn(CC3CC4(CO3)C(=O)Nc3ccccc34)nn2)nc1C]

(AB-F) Ethyl-1-((2'-oxo-4,5-dihydro-2H-spiro[furan-3,3'-indoline]-5-yl)methyl)-1H-1,2,3-triazole-4-carboxylate

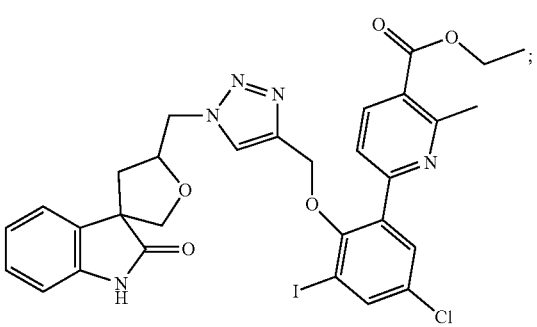 [SMILES: CCOC(=O)c1ccc(-c2cc(Cl)cc(I)c2OCc2cn(CC3CC4(CO3)C(=O)Nc3ccccc34)nn2)nc1C]

(AB-C) 5-((4-Phenyl-1H-1,2,3-triazol-1-yl)methyl)-4,5-dihydro-2H-spiro[furan-3,3'-indolin]-2'-one

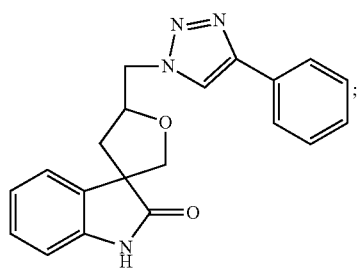 [SMILES: O=C1Nc2ccccc2C12COC(Cn1cc(-c3ccccc3)nn1)C2]

(AB-G) 5-((4-(Hydroxymethyl)-1H-1,2,3-triazol-1-yl)methyl)-4,5-dihydro-2H-spiro[furan-3,3'-indolin]-2'-one

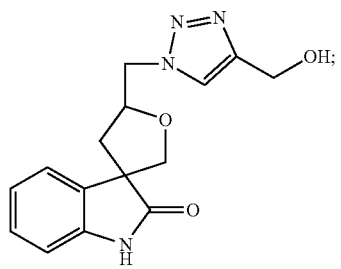

(AB-E) 5-((4-(2-Hydroxypropan-2-yl)-1H-1,2,3-triazol-1-yl)methyl)-4,5-dihydro-2H-spiro[furan-3,3'-indolin]-2'-one

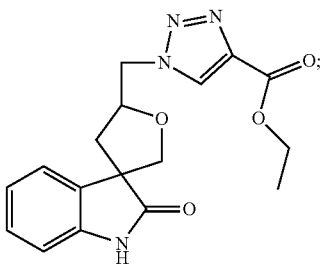 [SMILES: CCOC(=O)c1cn(CC2CC3(CO2)C(=O)Nc2ccccc23)nn1]

and (AB-D) 5-((4-(4-Nitrophenyl)-1H-1,2,3-triazol-1-yl)methyl)-4,5-dihydro-2H-spiro[furan-3,3'-indolin]-2'-one

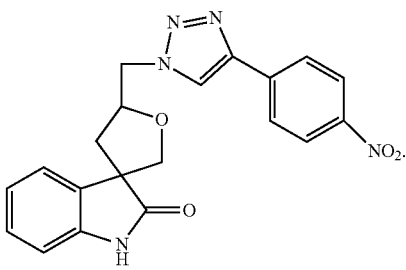 [SMILES: O=C1Nc2ccccc2C12COC(Cn1cc(-c3ccc([N+](=O)[O-])cc3)nn1)C2]

4. The compound as claimed in claim 1, represented by the formula III:

Formula III

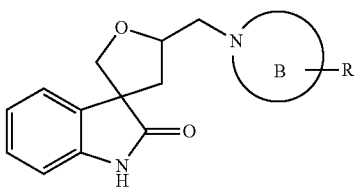

wherein ring B is a cyclic amine optionally internally substituted with one or more hetero atoms and substituted with a single substituent R, wherein R is hydrogen, alkoxy, aryloxy, hydroxy, alkoxycarbonyl, amide, amino, alkyl, phenyl, pyridinyl, benzyl, or benzoyl;

R is optionally substituted with one or more substituents $R^a$, wherein $R^a$ is halogen, hydroxy, alkoxy, alkyl, phenyl, pyridinyl, benzyl, benzoyl, aryloxy, nitro, cyano, alkoxycarbonyl, or aldehyde;

each $R^a$ is optionally substituted with one or more of substituents $R^b$, wherein $R^b$ is halogen, hydroxy, alkoxy, alkyl, phenyl, pyridinyl, benzyl, benzoyl, aryloxy, nitro, cyano, alkoxycarbonyl, or aldehyde; and each $R^b$ is optionally substituted with one or more substituents $R^c$, wherein $R^c$ is alkoxycarbonyl, halogen or alkyl.

5. The compound as claimed in claim 1, selected from the group consisting of:

(AB-X) 5-((4-Phenylpiperazin-1-yl)methyl)-4,5-dihydro-2H-spiro[furan-3,3'-indolin]-2'-one

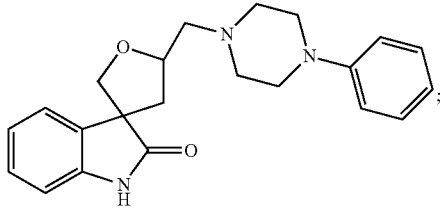

(AB-K) 5-(Morpholinomethyl)-4,5-dihydro-2H-spiro[furan-3,3'-indolin]-2'-one

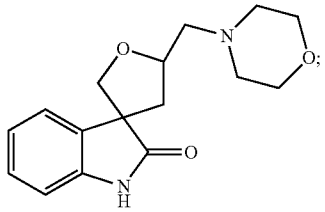 [SMILES: O=C1Nc2ccccc2C12COC(CN1CCOCC1)C2]

(AB-S) 5-((4-(Pyridin-2-yl)piperazin-1-yl)methyl)-4,5-dihydro-2H -spiro[furan-3,3'-indolin]-2'-one

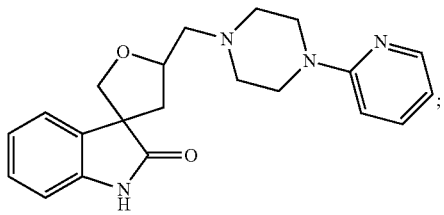 [SMILES: O=C1Nc2ccccc2C12COC(CN1CCN(c3ccccn3)CC1)C2]

(AB-U) 5-((4-(2-Methoxyphenyl)piperazin-1-yl)methyl)-4,5-dihydro-2H-spiro[furan-3,3'-indolin]-2'-one

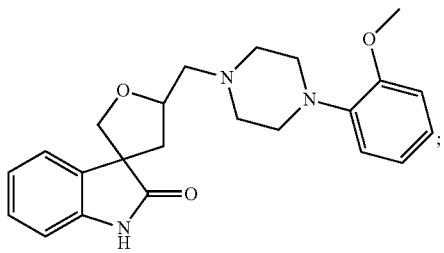 [SMILES: COc1ccccc1N1CCN(CC2CC3(CO2)C(=O)Nc2ccccc23)CC1]

(AB-T) 5-((4-(4-Methoxyphenyl)piperazin-1-yl)methyl)-4,5-dihydro-2H-spiro[furan-3,3'-indolin]-2'-one

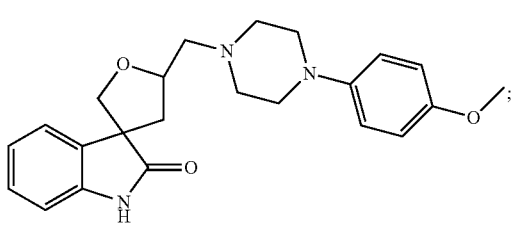 [SMILES: COc1ccc(N2CCN(CC3CC4(CO3)C(=O)Nc3ccccc34)CC2)cc1]

(AB-Q) 5-((4-Benzoylpiperazin-1-yl)methyl)-4,5-dihydro-2H-spiro[furan-3,3'-indolin]-2'-one

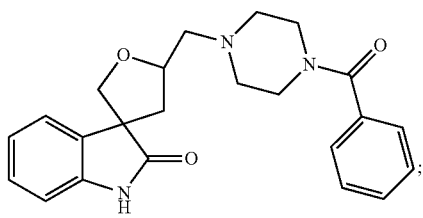 [SMILES: O=C(c1ccccc1)N1CCN(CC2CC3(CO2)C(=O)Nc2ccccc23)CC1]

(AB-L) 5-(Thiomorpholinomethyl)-4,5-dihydro-2H-spiro[furan-3,3'-indolin]-2'-one

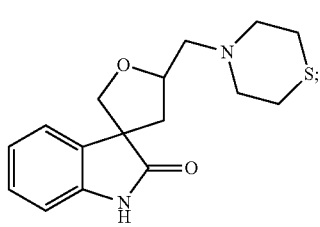 [SMILES: O=C1Nc2ccccc2C12COC(CN1CCSCC1)C2]

(AB-R) 5((4-Benzylpiperazin-1-yl)methyl)-4,5-dihydro-2H-spiro[furan-3,3'-indolin]-2'-one

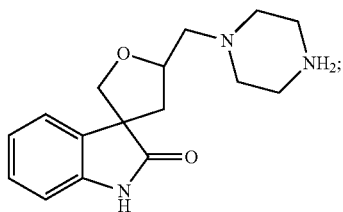

or (AB-V) 5-((4-(Bis(4-fluorophenyl)methyl)piperazin-1-yl)methyl)-4,5-dihydro-2H-spiro[furan-3,3'-indolin]-2'-one

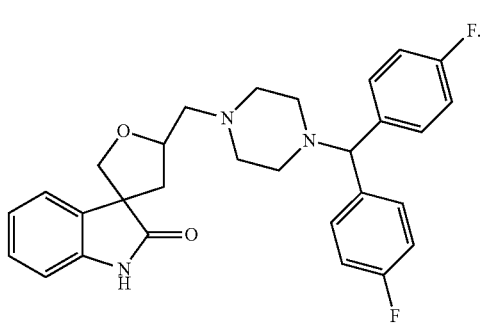 [SMILES: O=C1Nc2ccccc2C12COC(CN1CCN(C(c3ccc(F)cc3)c3ccc(F)cc3)CC1)C2]

6. The compound as claimed in claim 1, represented by formula IV:

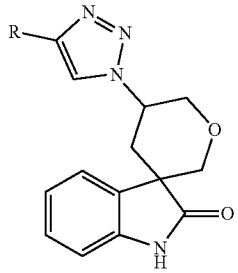

Formula IV wherein
R is hydrogen, alkoxy, aryloxy, hydroxy, alkoxycarbonyl, amide, amino, alkyl, phenyl, pyridinyl, benzyl, or benzoyl;
R is optionally substituted with one or more of substituents $R^a$, wherein $R^a$ is halogen, hydroxy, alkoxy, alkyl, phenyl, pyridinyl, benzyl, benzoyl, aryloxy, nitro, cyano, alkoxycarbonyl, or aldehyde;
each $R^a$ is substituted with one or more substituents $R^b$, wherein $R^b$ is halogen, hydroxy, alkoxy, alkyl, phenyl, pyridinyl, benzyl, benzoyl, aryloxy, nitro, cyano, alkoxycarbonyl, or aldehyde; and
each $R^b$ is optionally substituted with one or more substituents $R^c$, wherein $R^c$ is alkoxycarbonyl, halogen or alkyl.

7. The compound as claimed in claim 1, selected from the group consisting of:
(AC-A) Ethyl 6-(5-fluoro-2-((1-(2-oxo-2', 4', 5', 6'-tetrahydrospiro[indoline-3,3'-pyran]-5'-yl)-1H-1,2,3-triazol-4-yl)methoxy)-phenyl)-2-methylnicotinate

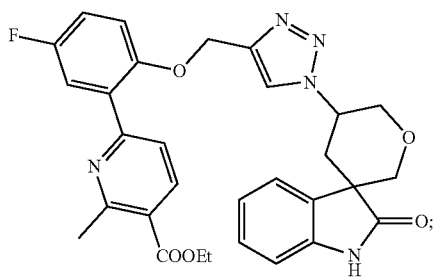 [SMILES: CCOC(=O)c1ccc(-c2cc(F)ccc2OCc2cn(C3COCC4(C3)C(=O)Nc3ccccc34)nn2)nc1C]

(AC-B) Ethyl 2-methyl-6-(2-((1-(2-oxo-2',4',5',6'-tetrahydrospiro[indoline-3,3'-pyran]-5'-yl)-1H-1,2,3-triazol-4-yl)methoxy)-phenyl)nicotinate

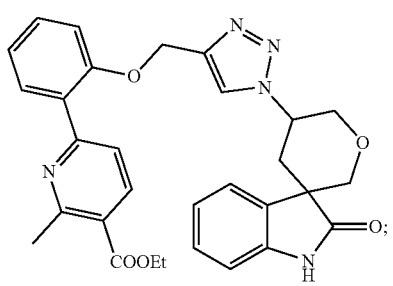 [SMILES: CCOC(=O)c1ccc(-c2ccccc2OCc2cn(C3COCC4(C3)C(=O)Nc3ccccc34)nn2)nc1C]

(AC-C) Ethyl 6-(5-chloro-2-((1-(2-oxo-2',4',5',6'-tetrahydrospiro [indoline-3,3'-pyran]-5'-y1)-1H-1,2,3-triazol-4- yl)methoxy)-phenyl)-2-methyl nicotinate

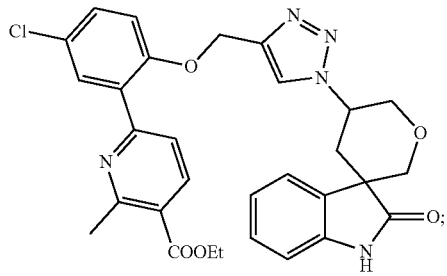 [SMILES: CCOC(=O)c1ccc(-c2cc(Cl)ccc2OCc2cn(C3COCC4(C3)C(=O)Nc3ccccc34)nn2)nc1C]

(AC-D) Ethyl 6-(3,5-dichloro-2-((1-(2-oxo-2',4',5',6'-tetrahydrospiro-[indoline-3,3'-pyran]-5'-yl)-1H-1,2,3-triazol-4-yl)methoxy)phenyl)-2-methyl nicotinate

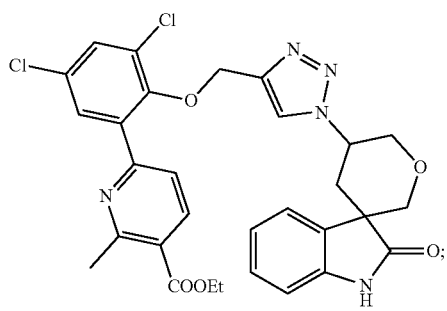 [SMILES: CCOC(=O)c1ccc(-c2cc(Cl)cc(Cl)c2OCc2cn(C3COCC4(C3)C(=O)Nc3ccccc34)nn2)nc1C]

(AC-E) 2-((1-(2-Oxo-2', 4', 5', 6'-tetrahydrospiro[indoline-3,3'-pyran]-5'-yl)-1H-1,2,3-triazol-4-yl) methoxy) benzaldehyde

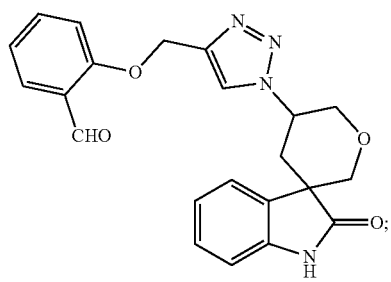 [SMILES: O=Cc1ccccc1OCc1cn(C2COCC3(C2)C(=O)Nc2ccccc23)nn1]

(AC-F) 5'-(4-(Pyridin-2-yl)- 1H-1,2,3-triazol-1-yl)-2',4', 5',6'-tetrahydrospiro[indoline-3,3'-pyran]-2-one

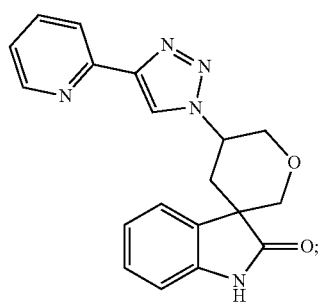 [SMILES: O=C1Nc2ccccc2C12COCC(n1cc(-c3ccccn3)nn1)C2]

(AC-G) 5'-(4-(Hydroxy(phenyl)methyl)-1H-1,2,3-triazol-1-yl)-2',4',5',6'-tetrahydro spiro[indoline-3,3'-pyran]-2-one

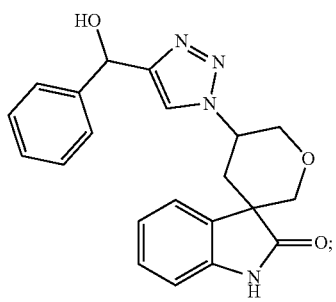 [SMILES: O=C1Nc2ccccc2C12COCC(n1cc(C(O)c3ccccc3)nn1)C2]

(AC-H) 5'-(4-((2-Nitrophenoxy)methyl)-1H-1,2,3-triazol-1-yl)-2',4',5',6'-tetrahydro Spiro -[indoline-3,3'-pyran]-2-one

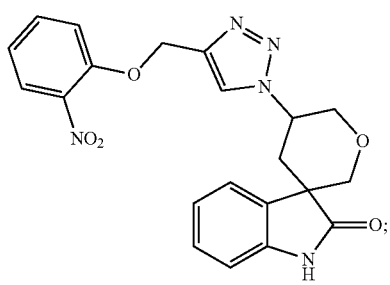 [SMILES: O=C1Nc2ccccc2C12COCC(n1cc(COc3ccccc3[N+](=O)[O-])nn1)C2]

(AC-I) 5'-(4-((4-Chloro-2-methylphenoxy)methyl)-1H-1,2,3-triazol-1-yl)-2',4',5',6'-tetra hydrospiro[indoline-3,3'-pyran]-2-one

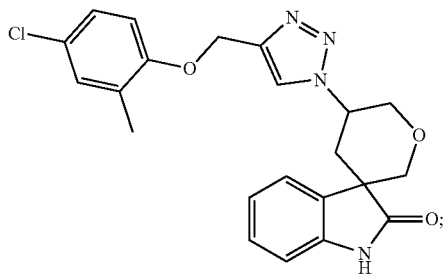 [SMILES: Cc1cc(Cl)ccc1OCc1cn(C2COCC3(C2)C(=O)Nc2ccccc23)nn1]

(AC-J) 5'-(4-((3-Hydroxyphenylamino)methyl)-1H-1,2,3-triazol-1-yl)-2',4',  ',6'-tetrahydrospiro[indoline-3,3'-pyran]-2-one

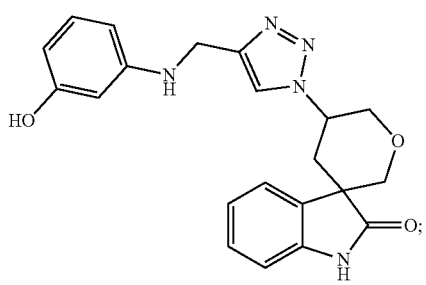 [SMILES: O=C1Nc2ccccc2C12COCC(n1cc(CNc3cccc(O)c3)nn1)C2]

(AC-K) 5'-(4-((3-Aminophenoxy)methyl)-1H-1,2,3-triazol-1-yl) -2',4',5',6'-tetrahydro spiro[indoline-3,3'-pyran]-2-one

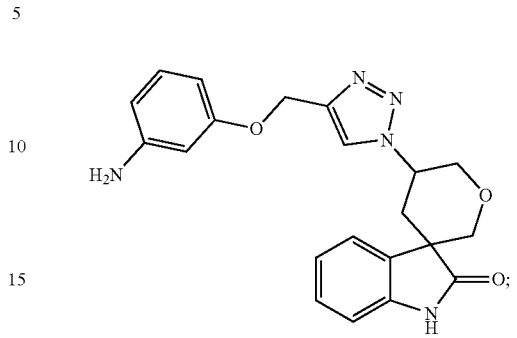

or (AC-L) 5'-(4-((5-Bromo-3-nitropyridin-2-yloxy)methyl)-1H-1,2,3-triazol-1-yl)-2',4',5',6'-tetrahydrospiro[indoline-3,3'-pyran]-2-one

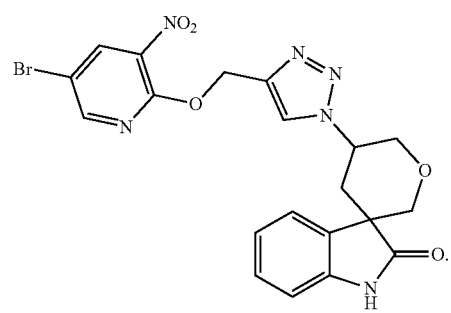 [SMILES: O=C1Nc2ccccc2C12COCC(n1cc(COc3ncc(Br)cc3[N+](=O)[O-])nn1)C2]

8. A process for the preparation of a compound of claim 1 comprising the steps of:

a) allylation of oxindole;

b) protection of free amine groups in said oxindole with a boc group;

c) formylation of the product of (b) using formaldehyde;

d) removal of said boc group to give a free amine;

e) cyclisation of the product of (d) with iodine to give a spiro-iodo compound;

f) azidating said spiro-iodo compound with sodium azide to give a spiro-azide compound or reacting said spiro-iodo compound with a cyclic amine to give a cyclic amine based spirooxindole;

g) reacting the product of (f) with an alkyne to give a triazole based spirooxindole under click chemistry conditions.

9. A method for inhibiting GSK3β activity comprising administering an amount of the compound of claim 1 to a subject sufficient to inhibit GSKβ activity.

10. A method for treating pancreatic cancer comprising administering to a subject with pancreatic cancer, an amount of the compound of claim 1 to inhibit GSK3β activity.

* * * * *